United States Patent [19]

Kelln et al.

[11] Patent Number: 5,292,484
[45] Date of Patent: Mar. 8, 1994

[54] CUVETTE AND CUVETTE CARTRIDGE FOR A CHEMICAL ANALYZER

[75] Inventors: Norman Kelln; Thomas Tiffany, both of Spokane; Robin Olson, Veradale; Bruce Weyrauch, Newman Lake, all of Wash.

[73] Assignees: Spectrum Systems, Inc., Spokane, Wash.; Schiapparelli Biosystems, Inc., Fairfield, N.J.

[21] Appl. No.: 916,040

[22] Filed: Jul. 16, 1992

[51] Int. Cl.$^5$ .................. B01L 3/00; G01N 21/00; G01N 1/10
[52] U.S. Cl. .................. 422/102; 422/58; 422/63; 422/64; 422/82.05; 422/82.09; 422/104; 356/246
[58] Field of Search .................. 422/58, 64, 63, 102, 422/82.05, 82.09, 104; 356/246

[56] References Cited

U.S. PATENT DOCUMENTS

| | | | |
|---|---|---|---|
| 3,994,594 | 11/1976 | Sandrock et al. | 356/246 |
| 4,123,173 | 10/1978 | Bullock et al. | 356/246 |
| 4,126,418 | 11/1978 | Krasnow | 422/64 |
| 4,178,345 | 12/1979 | Terk | 422/61 |
| 4,195,060 | 3/1980 | Terk | 422/61 |
| 4,338,279 | 7/1982 | Orimo et al. | 422/64 |
| 4,634,575 | 1/1987 | Kawakami et al. | 422/63 |
| 4,636,477 | 1/1987 | Ronka et al. | 436/48 |
| 4,764,342 | 8/1988 | Kelln et al. | 422/72 |
| 4,844,887 | 7/1989 | Galle et al. | 422/65 |
| 5,098,661 | 3/1992 | Froehlich et al. | 422/102 |

Primary Examiner—James C. Housel
Assistant Examiner—N. Bhat
Attorney, Agent, or Firm—Wells, St. John, Roberts, Gregory & Matkin

[57] ABSTRACT

A disposable cuvette is molded of rigid transparent plastic resin that is impervious to liquids to be handled within it. The cuvette has a rectangular cross section. Identical side walls extend between upper and lower ends of each cuvette, the upper end being open for reception of liquids and the lower end being closed. Recessed optical surface areas at the lower end are perpendicular to one another for optical testing of the cuvette contents. An elongated cartridge holds a stack of abutting cuvettes to facilitate their handling.

14 Claims, 17 Drawing Sheets

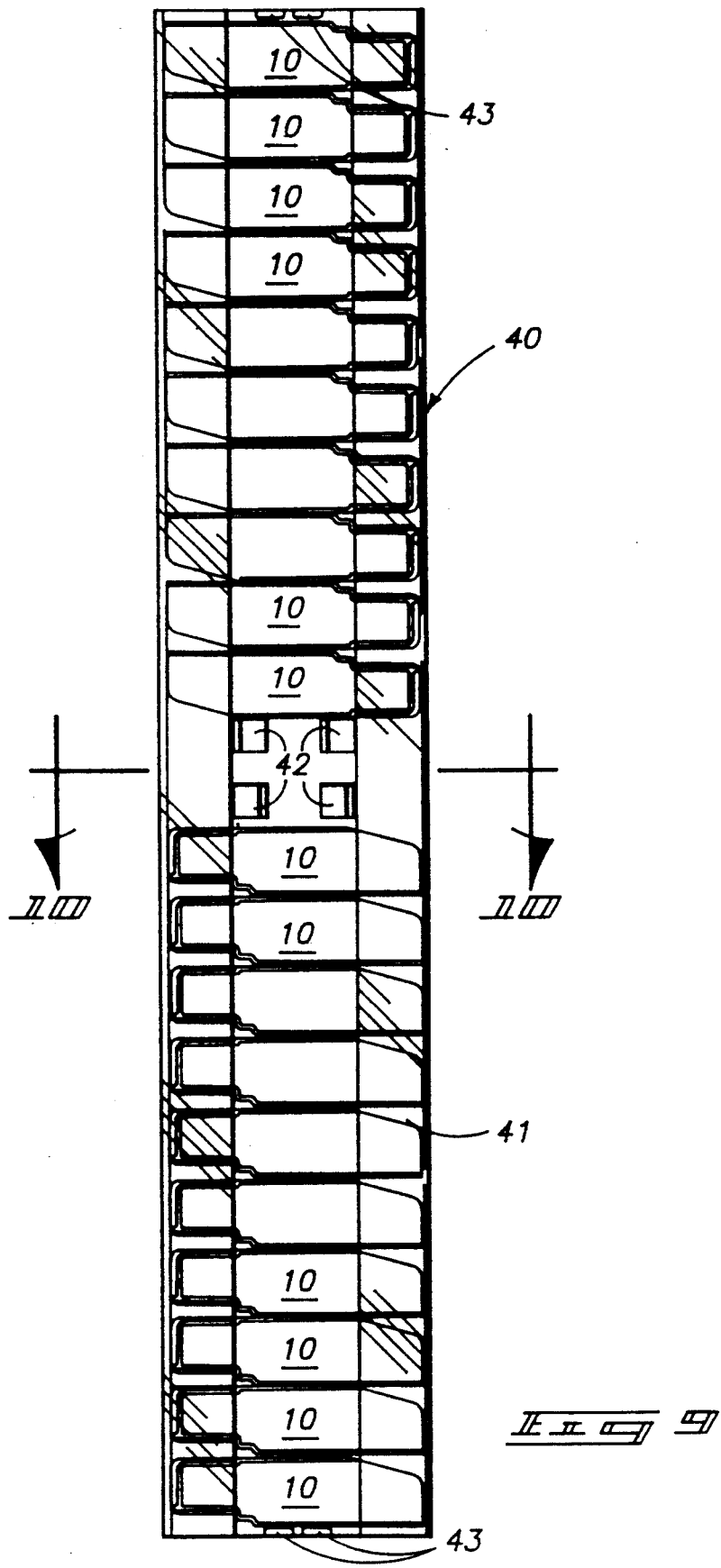

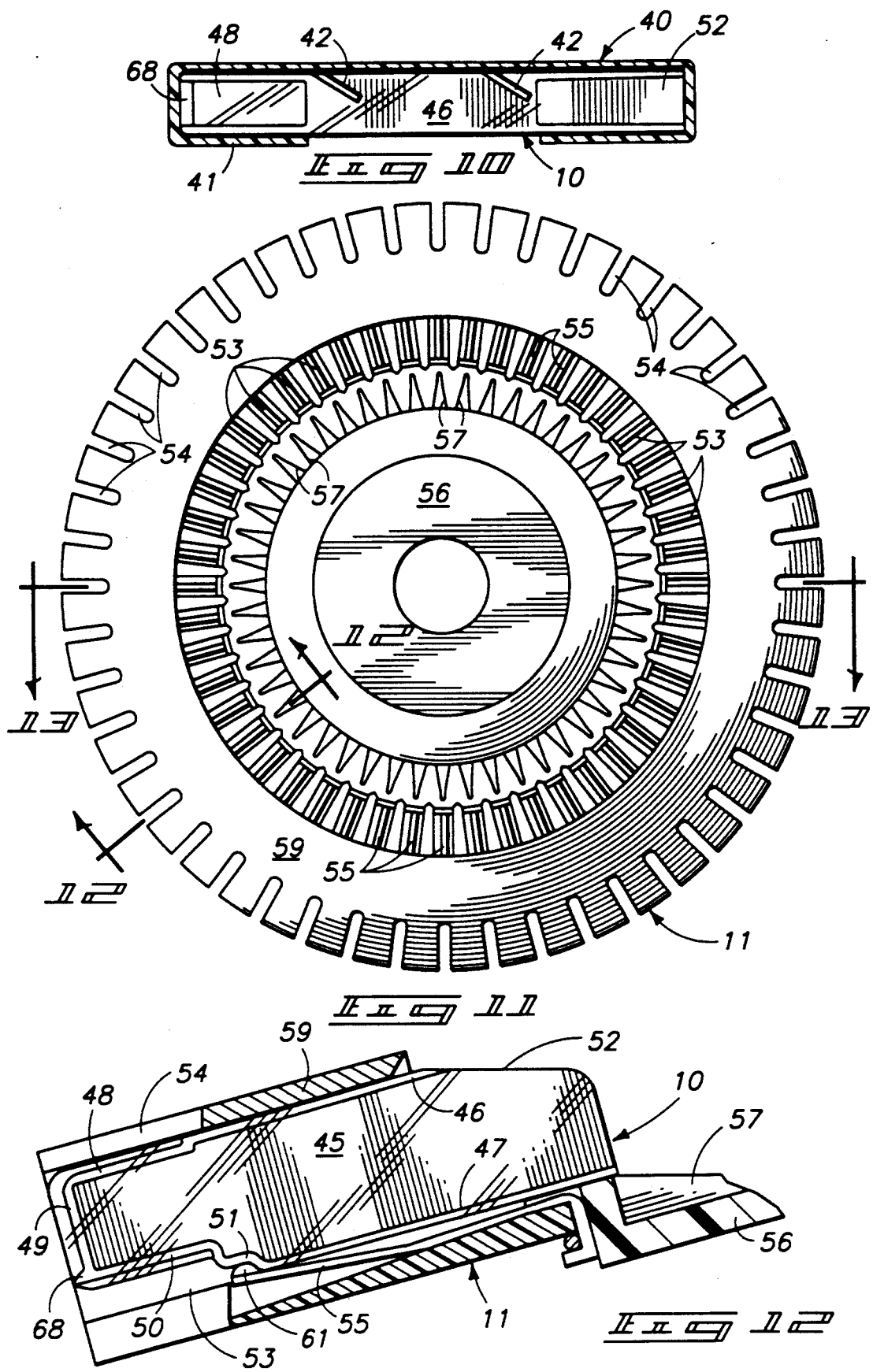

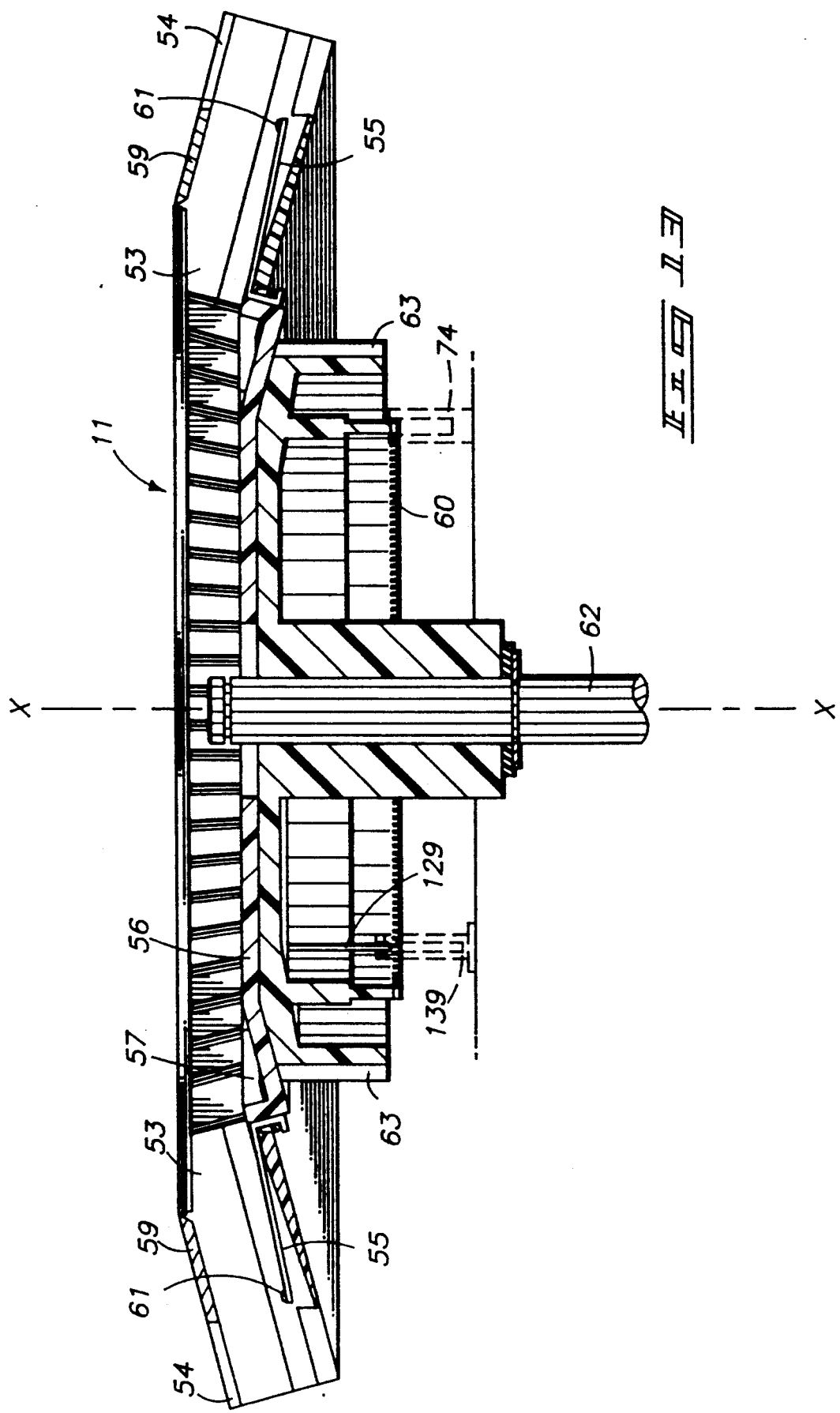

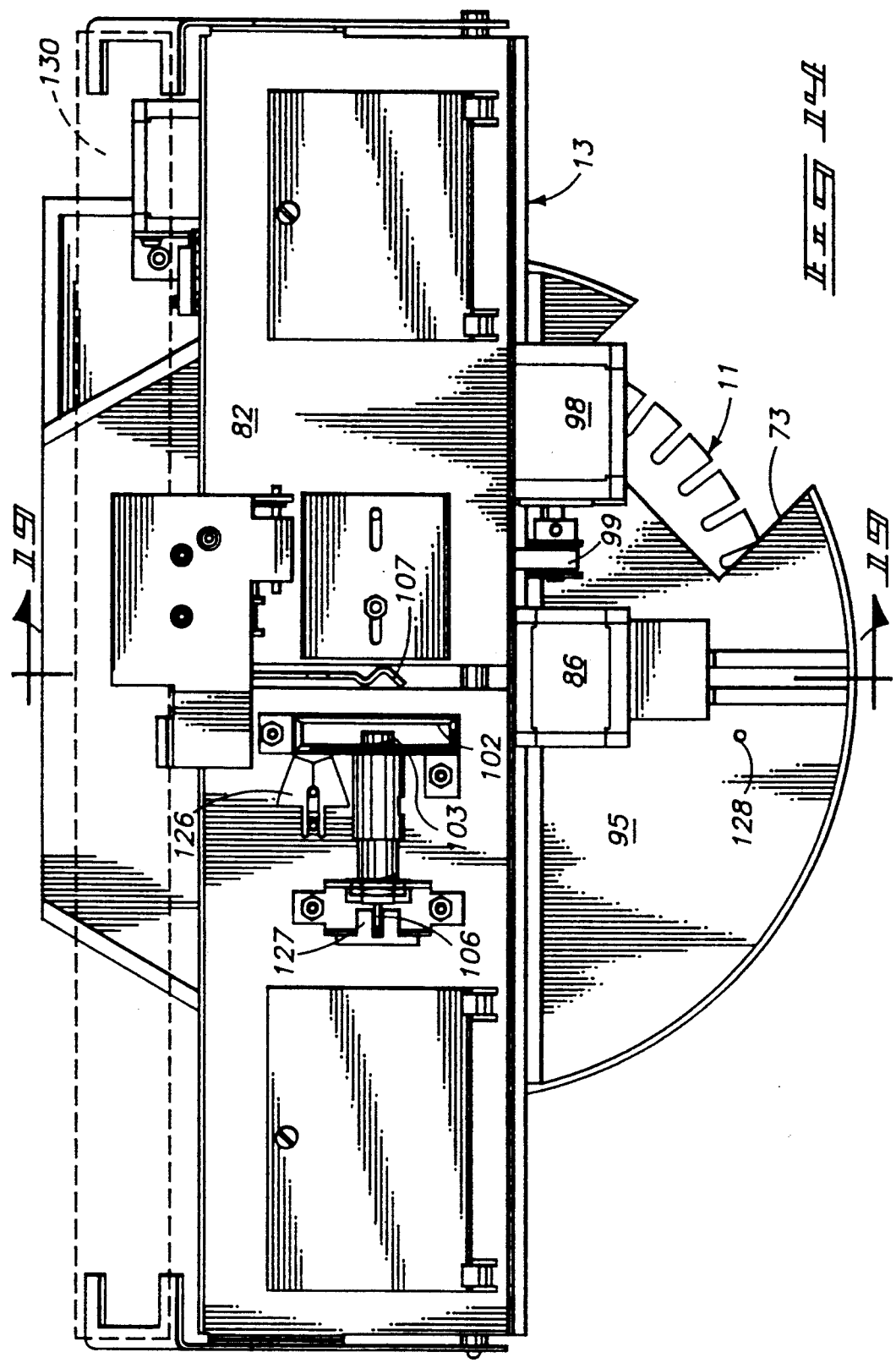

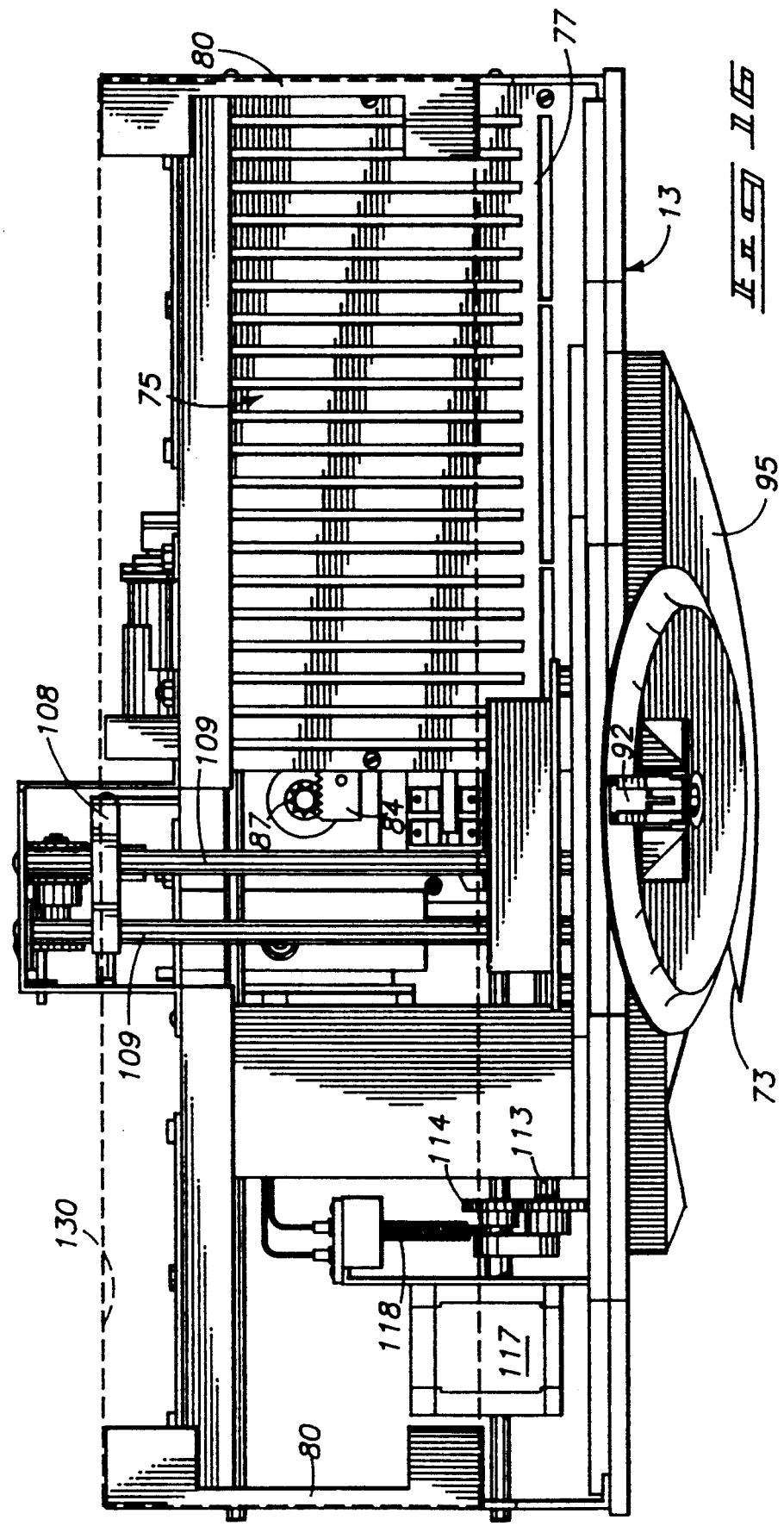

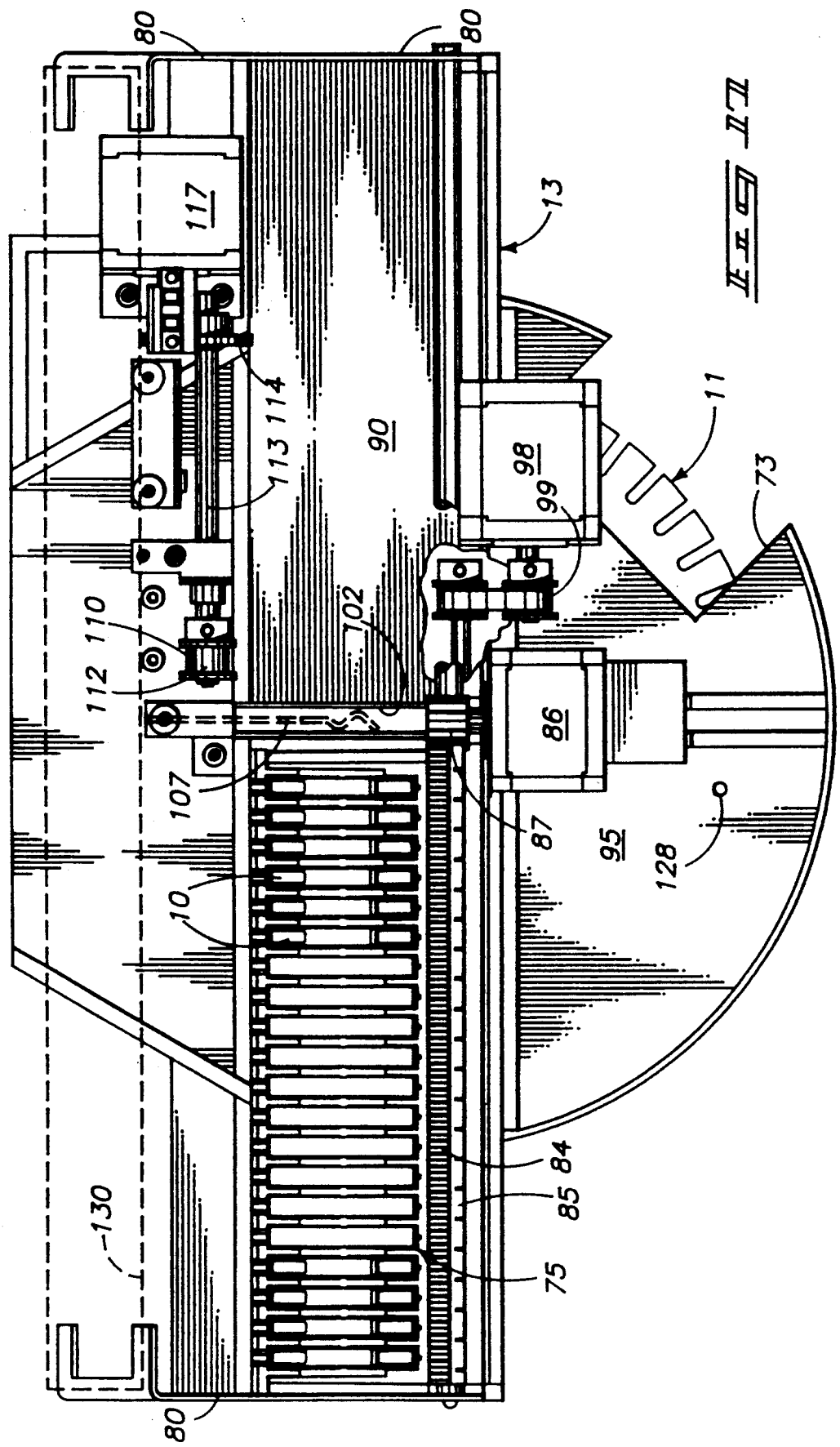

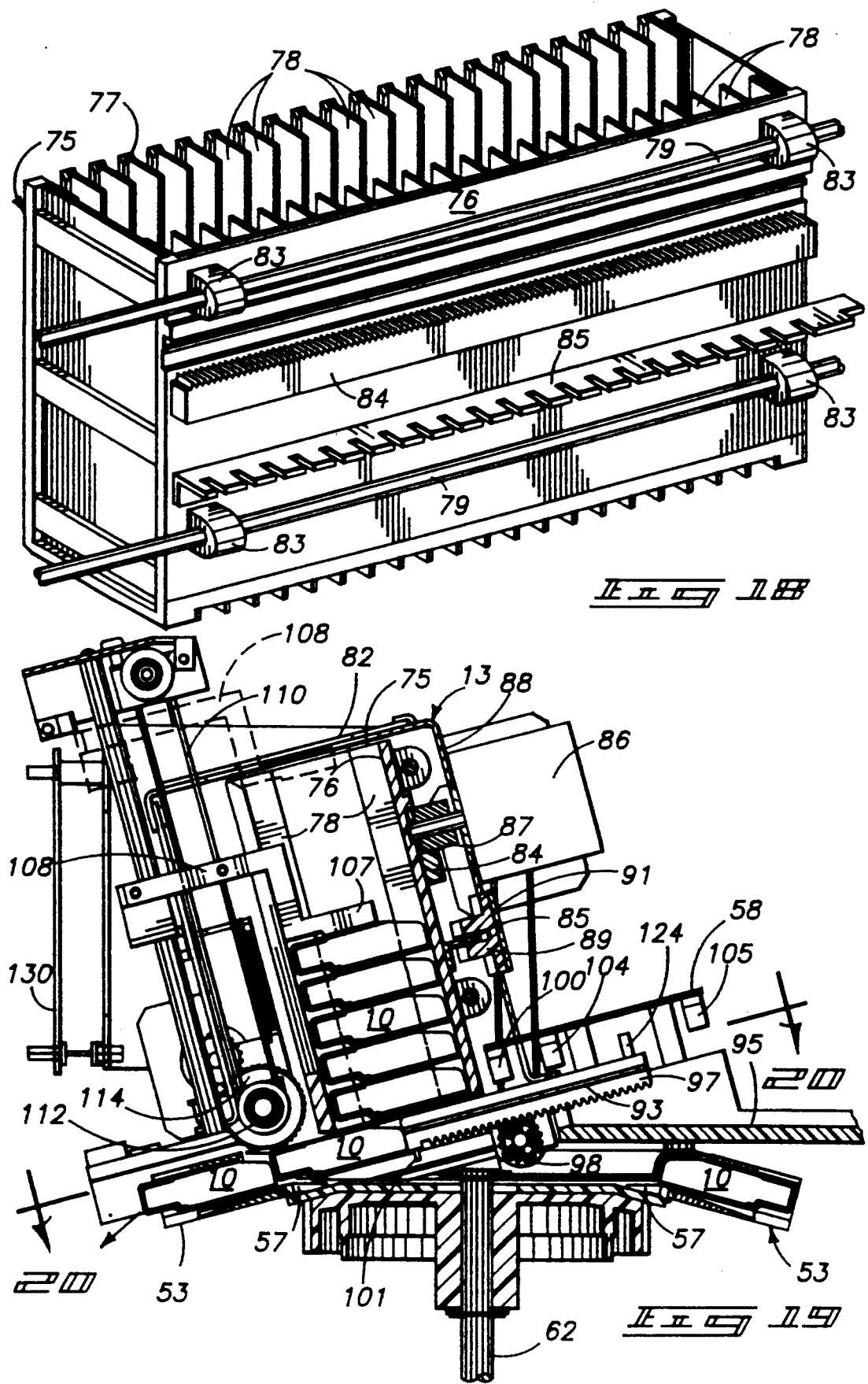

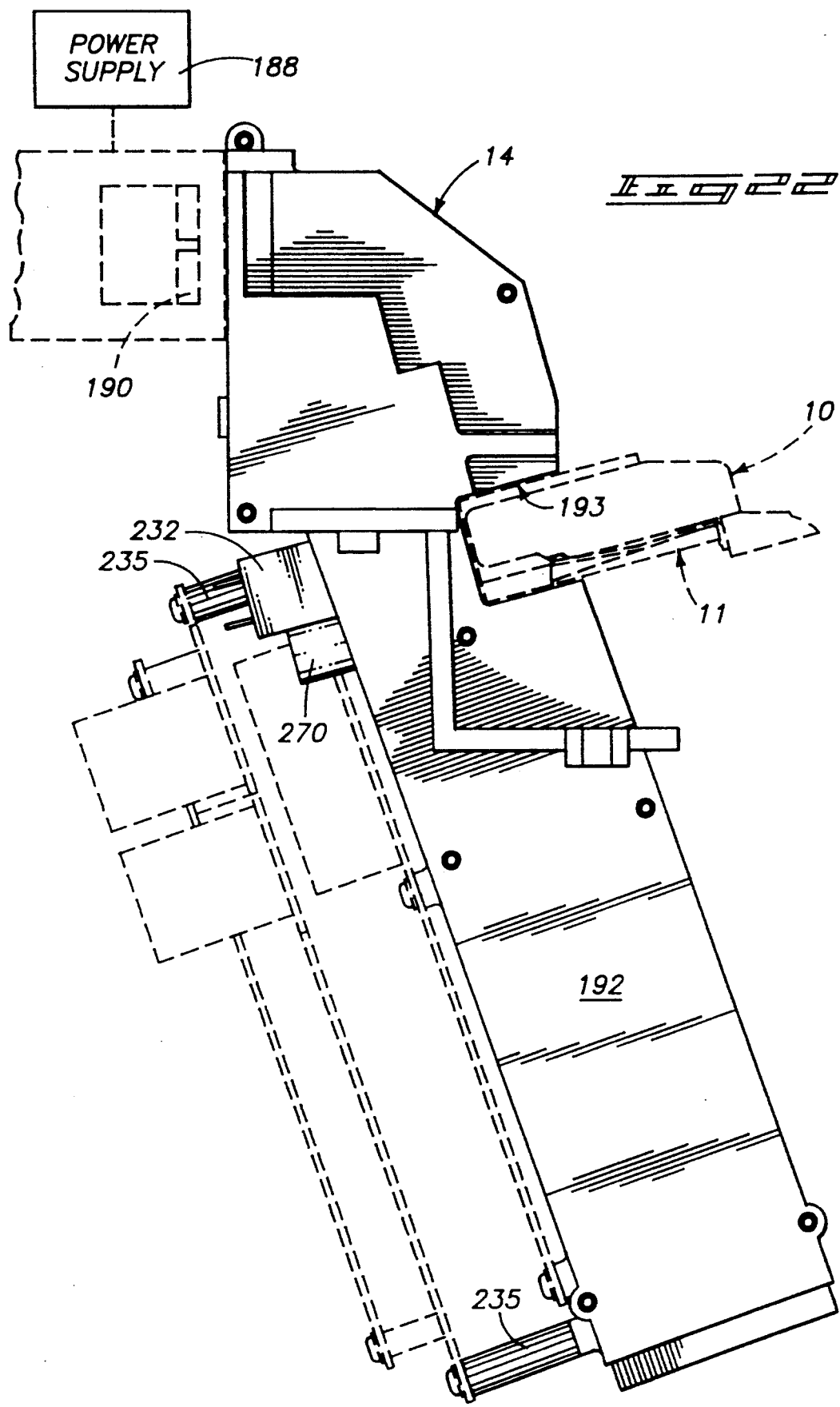

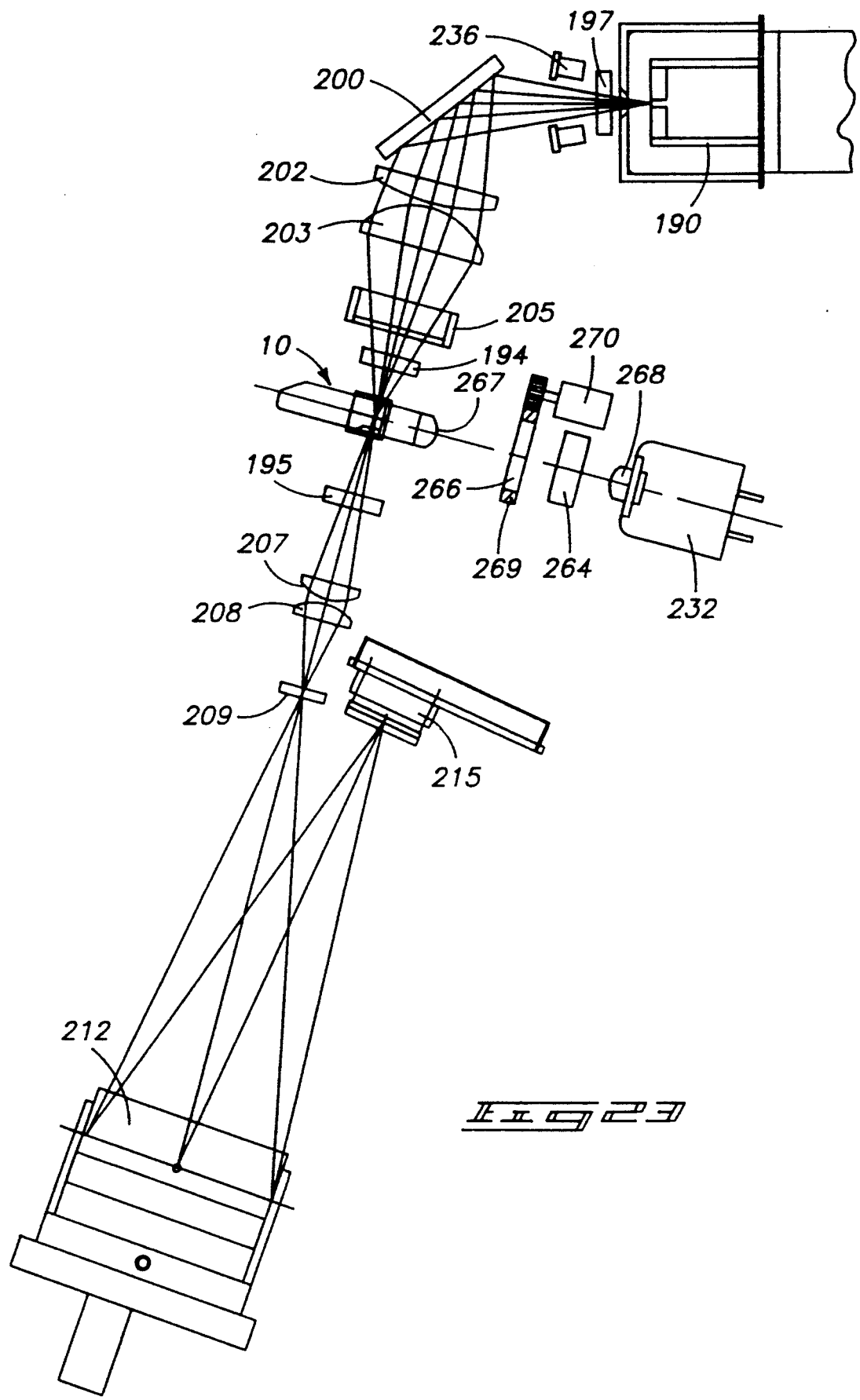

CUVETTE AND CUVETTE CARTRIDGE FOR A CHEMICAL ANALYZER

TECHNICAL FIELD

This disclosure pertains to a cuvette designed for use in a clinical chemistry analyzer for the testing of patient samples, such as blood or urine. It generally relates to automatic chemical analyzers for directly measuring properties of reacted liquids by photometric systems to determine optical absorbency and/or fluorescence of samples, thus producing qualitative and quantitative analyses of tested samples.

BACKGROUND OF THE INVENTION

Automated analyzers have been developed for biochemical analysis of patient samples, such as whole blood, serum, urine, plasma and cerebral spinal fluid. Most such equipment available today is complicated to operate, large and high in cost.

The operation of such equipment is technically complicated. It typically requires specialized operators to be always available, with commensurate personnel expenses being encountered. It is usually designed for use by large laboratories serving a wide geographic area or by a large medical facility. These existing analyzers carry out tests in a defined sequence of operations designed for efficient, high volume usage.

Such large scale capacity is not always required, particularly in smaller medical clinics where large volumes of blood samples are not encountered on a daily basis. The present chemical analyzer was developed to meet the practical needs of smaller medical settings. It is designed as a desk-top unit that can be operated without specialized laboratory training. Its capacity is adequate for meeting typical clinical applications. As an example, it can produce a maximum of 164 test results per hour for routine, single reagent chemistries. To provide a representative wide number of reagents, the analyzer can handle forty reagent containers of two different sizes. Its capacity can be effectively doubled by using two of the chemistry instruments in tandem, both being controlled by a common workstation.

The compact nature of the analyzer can be partially attributed to the fact that a single probe arm and pipette service all of the functional liquid-handling components included within it. The common pipette is used for transferring samples and reagents, as well as for diluting liquids as needed by particular test requirements.

To obtain large volumes of tests, conventional laboratory analyzers are programmed to conduct test procedures in a fixed sequence of events. While predetermined test sequences are practical in high volume chemical analyzer applications, there is a need for more flexible operation when scaling such test procedures to meet the needs of smaller medical facilities.

The present invention provides testing flexibility by permitting random access to each cuvette on a test turntable and to each container (cups, wells and reagent bottles) on a sample/reagent tray. It is unnecessary for the instrument to sequence through any predetermined processing steps. The controlling software can tailor the required steps to the test currently requisitioned. This permits a greater number of tests to be conducted while using a minimum number of containers, cuvettes and reagent bottles. The software controls the sequencing of tests based upon predetermined priority schedules, rather than defined test sequences dictated by the nature of the tests being conducted.

Increased versatility is also provided in the present chemical analyzer by providing the capability of inserting pre-loaded reagents within cuvettes. The pre-loaded cuvettes are fed to a dispensing magazine that directs them to the turntable. Random access can be provided to a plurality of stacks of incoming cuvettes. Some can be preloaded and some can be empty. This provides the capability of random access to prepackaged chemistry involving powdered or solid reagents to supplement the liquid reagents available on the sample/reagent tray.

Disposable cuvettes are provided automatically within the analyzer by a cuvette dispenser. Reloading of the cuvettes into a dispensing magazine included in the chemistry instrument is physically organized to meet the supply needs of the instrument with minimum cuvette handling by the operator.

A reaction turntable can handle a maximum of 48 cuvettes at any given time. Both absorbance and fluorescence polarization tests can be carried out on samples within selected cuvettes through use of a single optical system.

Further details about the system will be clear from the following description.

BRIEF DESCRIPTION OF THE DRAWINGS

One or more preferred forms of the invention are described with reference to the accompanying drawings. The drawings are briefly described below.

FIG. 9 is a front elevation view of a loaded cuvette cartridge;

FIG. 10 is a transverse sectional view through a loaded cartridge as seen along line 10—10 in FIG. 9;

FIG. 12 is an enlarged sectional view taken along line 12—12 in FIG. 11;

FIG. 13 is a transverse sectional view through the turntable as seen along line 13—13 in FIG. 11.

FIG. 14 is a plan view of the cuvette delivery module;

FIG. 15 is a front elevation view taken parallel to the side wall of the delivery module;

FIG. 16 is a similar rear elevation view, the turntable being removed;

FIG. 17 is a plan of the delivery module with its cover removed;

FIG. 18 is a perspective view of the cuvette magazine;

FIG. 19 is a transverse vertical sectional view of the delivery module as seen along line 19—19 in FIG. 14;

FIG. 22 is a side elevation view of the optical system enclosure; and

FIG. 23 is a diagrammatic view illustrating operation of the optical system.

DETAILED DESCRIPTION OF THE PREFERRED EMBODIMENT

Figure 1:
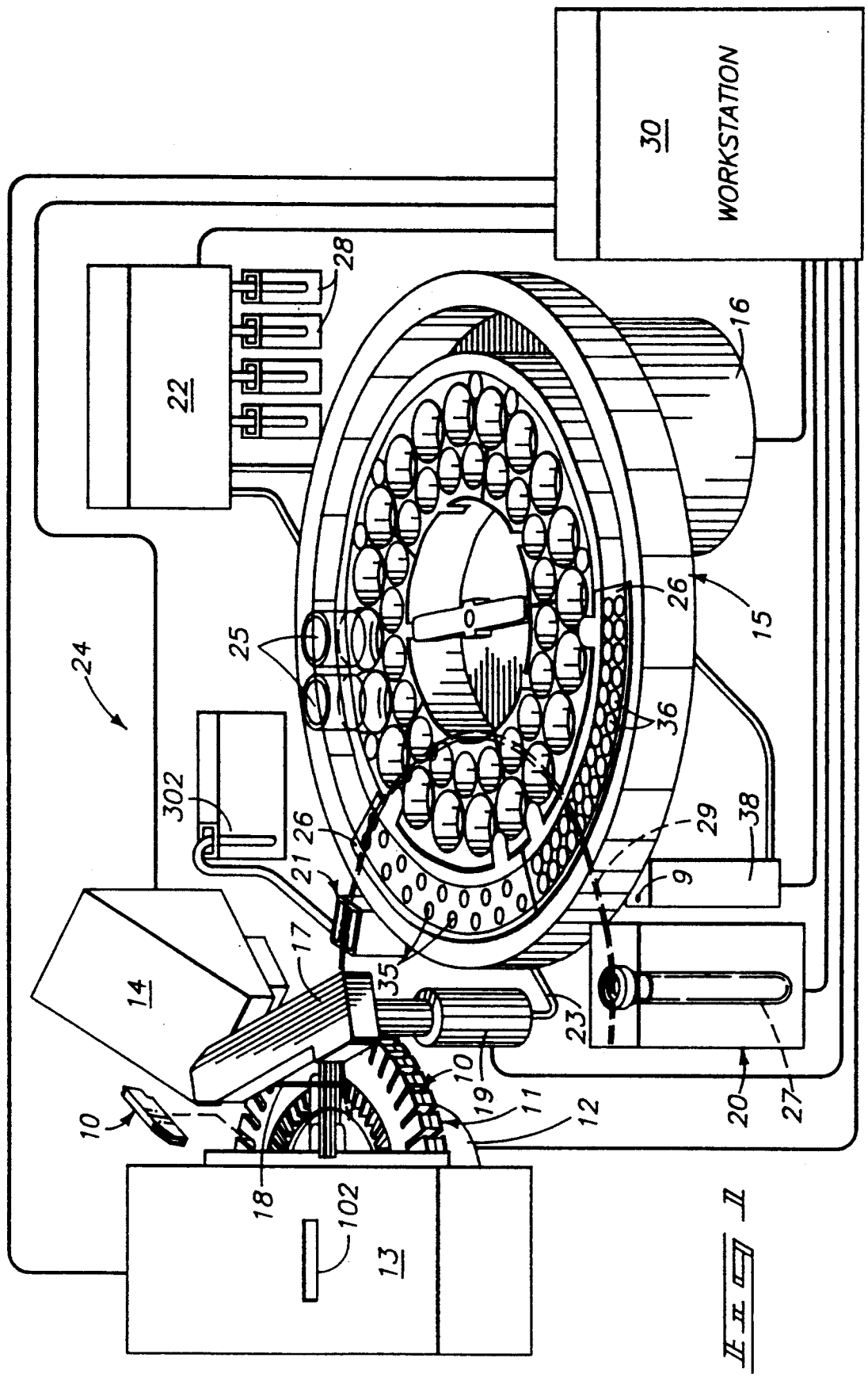
FIG. 1 is a diagrammatic perspective view of the principal components in the analyzer.

This disclosure of the invention is submitted in furtherance of the constitutional purposes of the U.S. Patent Laws "to promote the progress of science and useful arts" (Article 1, Section 8).

System Overview

The automatic chemical analyzer (generally illustrated in FIGS. 1-3) includes a turntable 11 rotatably mounted about a first vertical axis. A plurality of disposable cuvettes 10 are releasably mounted to the turntable 11. A first power means, shown as motor 12, is operably connected to turntable 11 for alternately (1) indexing it at a stationary angular position about the first axis with a selected cuvette 10 positioned at a cuvette access station A or (2) turning it about the first axis while mixing or centrifuging contents of cuvettes mounted to it.

First analytical means, illustrated as an optical system 14, is provided adjacent to the turntable 11 for performing tests on the contents of the cuvettes 10 as they rotate about the turntable axis.

A tray 15 is rotatably mounted about a second vertical axis parallel to and spaced from the first axis. A plurality of containers 25, 35, and 36 are positioned about tray 15 for reception of samples and reagent liquids. Second power means, illustrated as motor 16, is operably connected to the tray 15. The motor 16 indexes tray 15 to a stationary angular position about the second axis with a selected container positioned at a container access station C.

The analyzer also includes a probe arm 17 movable about a third vertical axis parallel to the first axis. Probe arm 17 supports a downwardly-extending open pipette 18. The vertical pipette 18 is movable along an arcuate path centered about the third axis and intersecting both the cuvette access station A and container access station C. It can move along the arcuate path in a random fashion to transfer liquid from a container positioned on the tray at the container access station C to a cuvette 10 positioned on the turntable 11 at the cuvette access station A. The arcuate path of the pipette 18 can be visualized along a protective groove 29 formed at the exterior of the enclosure 39 housing the chemistry instrument 24.

The illustrated embodiment of the clinical chemistry analyzer consists of two major components: a chemistry instrument 24 and a workstation 30. The chemical instrument accepts liquid patient samples for testing purposes, performs appropriate optical and/or potentiometric measurements on the samples, and communicates the resulting test data to workstation 30. Workstation 30 is used by the operator to enter data, control operation of instrument components, accept data generated by the instrument, manage and maintain system information, and generate visual and printed reports about assays and instrument performance.

The chemistry instrument 24 is a separate unit with minimal operator controls. Either one or two identical chemistry instruments 24 can be linked to a single workstation 30, as required in a particular setting. The chemistry instrument 24 can perform several types of analysis. These include routine chemistries, electrolytes, therapeutic drug monitoring, drugs of abuse in urine, and other specialized tests.

The liquid-handling components that make up the chemistry instrument 24 are housed within enclosure 39 (FIGS. 2-5). It separates along a peripheral parting line 37 defining a lower supporting base 33 and an upper hinged cover 34.

The principal modular components of the chemistry instrument 24 are diagrammatically illustrated in FIG. 1. The illustrated components are specifically designed for use in association with a specially designed liquid cuvette 10.

A computerized operator interface to the chemistry instrument 24 is provided through connections to the programmable workstation 30. Most of the operator interactions with the analyzer take place at workstation 30. It is an external desktop computer located near the chemistry instrument(s) 24. It uses an industry standard operating system and bus structure, plus a hard disk. It is also provided with a custom instrument interface board for each associated chemistry instrument.

Operations required for sample testing of cuvette contents are not carried out in any predetermined sequence dictated by insertion of a sample into the chemistry instrument 24. Instead, workstation 30 serves as random access control means operably connected to the turntable 11, tray 15 and probe arm 17 for selectively transferring liquid from any container on the tray 15 to any cuvette 10 on the turntable 11 according to defined logical priority rules programmed into the workstation.

Operations carried out within the chemistry instrument 24 are timed about a repetitious cycle of operations. Each cycle involves sequentially transferring liquids to an awaiting cuvette 10 on the turntable 11, mixing the liquids, and centrifuging them for test purposes.

A monitor 31 is included within workstation 30 to display data, messages and optional menus for the operator. A keyboard 32 is included for operator input of data and instructions. A printer (not shown) of conventional design can also be provided in the system to record tests results and reports as required.

A plurality of test cuvettes 10 are releasably located within a motor-controlled turntable 11. It is powered by a DC motor 12. Motor 12 can be accurately controlled to (1) selectively index turntable 11 at a chosen angular position about its vertical axis for access to a particular cuvette and/or insertion of new cuvettes or (2) intermittently or reversibly rotate turntable 11 about its axis for mixing the contents of the cuvettes or (3) spin turntable 11 for centrifuging the contents of the cuvettes during photometric analysis.

A liquid transfer module includes a single probe arm 17 movably supported on the instrument 24 about a vertical axis. The outer end of probe arm 17 carries a downwardly extending pipette 18. Pipette 18 is used for transferring liquids between various locations about the chemistry instrument. Its lower or outer end is open for receiving or discharging liquids.

Probe arm 17 is supported and powered by a positioning assembly 19. The positioning assembly 19 has two stepper motors—one for imparting rotational motion to probe arm 17 and one for imparting vertical motion to it. Positioning assembly 19 can selectively move probe arm 17 and pipette 18 both angularly and axially relative to the vertical axis of probe arm 17.

The tip or lower end of pipette 18, while in an elevated condition permitting angular movement about the chemistry instrument 24, projects slightly into an open arcuate groove 29 (FIGS. 2, 3) formed about the cover 34 of the instrument enclosure. Groove 29 is centered about the axis of probe arm 17 and is recessed within cover 34. It overlaps the bottom of pipette 18 to prevent its accidental engagement with the hands of an operator as the pipette travels from one station to the next. The protective overlap of the pipette tip eliminates the danger of accidently impaling adjacent personnel when pipette 18 is subsequently lowered.

A cuvette dispenser module 13 is arranged on the framework of the equipment in a position immediately above the turntable 11. It includes a storage magazine for a plurality of stacks of cuvettes 10. It also includes an apparatus for transferring individual cuvettes 10 from a randomly selectable stack within the magazine 75 to a receiving compartment on turntable 11. Used cuvettes 10 are discarded into a removable cuvette disposal container (not shown) as new cuvettes are delivered to the turntable 11 by operation of a reciprocating ram. The cuvette disposal container can be a bag or bin into which used cuvettes drop when ejected from turntable 11.

The optical system 14 is contained within a housing positioned next to turntable 11. Optical system 14 performs photometric tests on the contents of cuvettes 10 while they are being spun about the turntable axis. The optical system 14 measures both fluorescent emissions and light absorbance by cuvette contents within the turntable 11. Photometric test groups typically supported include routine chemistries, special proteins, therapeutic drugs, and drugs of abuse.

For absorbency tests, the optical system 14 measures radiation at 180 degrees to the incident light. Readings are made at several wavelengths on a diode array, but only those points requested in specified test parameters are processed by the instrument 24. System offsets are subtracted from the results and the sample signal is divided by a reference signal. The negative logarithm of this ratio is the absorbance.

When conducting fluorescent tests, emitted radiation at a wavelength longer than that of the source is measured at 90 degrees to the incident beam. System offsets are subtracted and the intensity is then normalized using a reference signal.

A sample/reagent tray 15 is rotatably mounted about a vertical axis parallel to and spaced from the axis of turntable 11. It is rotatably powered by a stepper motor 16. Tray 15 consists of a circular reagent bottle support surrounded by separate interlocking ring segments 26. The removable ring segments 26 are used to hold reagents and samples required for assay procedures during operation of chemistry instrument 24.

Tray 15 supports a plurality of liquid containers, namely the reagent bottles 25, open cups 35 and open wells 36. The interchangeable ring segments 26 have two alternate configurations. One includes apertures for removably supporting individual sample cups 35. The other includes a plurality of integrally molded sample wells 36.

The individually removable cups 35 serve as containers for test samples supplied to the instrument 24 by the operator within one or more cups within a ring segment 26. Wells 36 are used by the instrument components in conjunction with operation of probe arm 17 for aliquoting of samples from a draw tube and for sample dilution purposes. The probe arm 17 can selectively transfer liquids from one well 36 to a second well 36, from a cup 35 to a well 36, or from a reagent bottle 25 to a well 36.

Access to the sample/reagent tray 15 is provided by a hinged tray access cover 8 formed in the enclosure cover 34. More limited manual access to a single ring segment 26 located at the front of the chemistry instrument 24 is provided by a hinged segment access port 7, which is a sub-assembly of cover 8.

Figure 3:
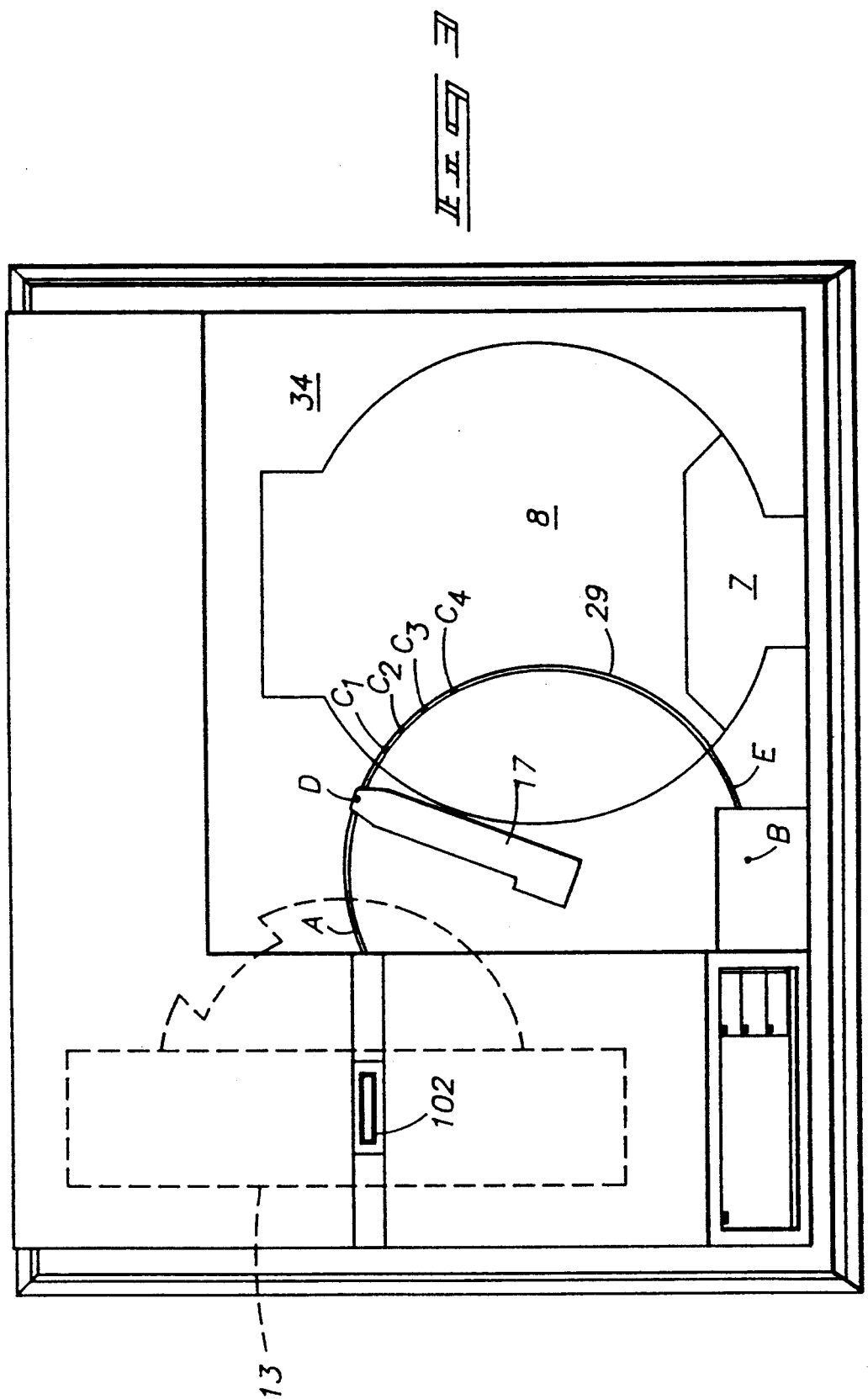
FIG. 3 is a plan view of the chemical instrument enclosure.

A stepper motor 16 can be operated to index sample/reagent tray 15 to a selected position about its axis with one or more selected containers at one of four container access stations shown in FIG. 3 at locations $C_1$, $C_2$, $C_3$, $C_4$ on the equipment framework. Each container access station intersects the path of pipette 18, which is coincident with groove 29.

Scanning means is provided next to the tray 15 for capturing identifying information from encoded indicia on a container positioned on it.

A cooling system (not shown) for the chemistry instrument 24 incorporates multiple thermoelectric cooling units. These are needed in the areas of the sample/reagent tray 15 and the turntable 11. Heat can be removed from the system by air exchange through a plurality of heat sinks.

A sample tube entry port 20 is provided on the framework for receiving and supporting successive individual draw tubes 27 as they are introduced into the instrument by the operator. Its primary use is to permit the taking of aliquots from positively identified, sealed patient draw tubes. It can also be used for delivery of control liquids from tubes of a similar exterior configuration, whether covered or open. Positive identification can be provided by an encoded label on each draw tube 27. The label is scanned by a bar code reader included within the sample tube entry port 20.

Each draw tube 27, of conventional design, is sealed by a closure at its upper end. Sample tube entry port 20 supports each manually inserted draw tube 27 while pipette 18 pierces the closure 162 to access liquid sample material from the tube interior. Liquid removal from successive tubes 27 occurs at a sample access station B along the arcuate path 29.

Puncturing means are provided within the sample tube entry port 20 for temporarily forming an opening through a closure on a manually-delivered draw tube 27 placed within it. A ram positioned below the puncturing means receives and coaxially orients a manually placed draw tube 27 relative to the puncturing means. It moves the draw tube parallel to a fourth vertical axis (centered along the puncturing means) between a lowered position wherein the draw tube 27 is clear of the puncturing means and a raised position wherein the puncturing means forms a temporary opening through the draw tube closure for subsequent coaxial insertion of the pipette 18. The interior of the draw tube 27 is then accessible by subsequently inserting pipette 18 coaxially through the puncturing means.

A wash/alignment module 21 is located at a fixed position on the framework. Its first purpose is to provide vertical basins within which the lower end surfaces of pipette 18 can be flushed clean during or after liquid transfer cycles. It also supports a conductive sensing plate that verifies both the radial alignment and elevational position of pipette 18 about the pipette axis on the probe arm 17 for monitoring alignment of the pipette. These operations occur at a wash/alignment station D along the arcuate path 29 of pipette 18.

A capacitive sensing circuit is operably connected to the pipette 18 and to conductive members located next to the tray 15 and within the sample tube entry port 20. The sensing circuit detects the level of liquid in a container on the tray or a draw tube 27 as it is approached by the pipette.

A second analytical means, shown as an Ion Specific Electrode (ISE) module 38 of conventional design and operation, is included within the chemistry instrument 24. It is illustrated generally in FIG. 1. Potentiometric tests may be requested and run by the ISE module 38 simultaneously with photometric tests being conducted by the optical system 14.

Samples are delivered to the ISE module 38 by pipette 18 at a sample delivery station E along the arcuate path 29 (FIG. 3). Module 38 can include tests for the presence of a variety of analytes, such as sodium, potassium, chloride, lithium or calcium. For each analyte, all sample types are analyzed in the same manner. The different sample types can be loaded using different dilution factors.

The ISE module 38 consists of electrodes specific to the chosen analyte, a reference electrode and the associated fluid system required to process tested samples. The potentiometric measurement consists of a voltage difference between the analyte's electrode and the reference electrode.

Water is supplied to pipette 18 from a syringe module 22 connected to a water supply container in a container rack 28. The syringe module 22 consists of a volume displacement syringe and associated valves leading to a source of water and a waste water container (not shown). It is used for all aspirations of samples, reagents and diluents in the chemistry instrument 24. The syringe module is of conventional design.

Tubing 23 (FIG. 1) connects syringe module 22 to pipette 18. Tubing 23 contains water that can be moved in opposite directions to receive or discharge liquids at the lower end of pipette 18.

The above components are individually operable under control of a distributed computerized controller system governed by the programmable workstation 30. Workstation 30 is electronically linked to the instrument via a bi-directional communications interface. This interface is used to communicate patient requisitions to the chemistry instrument 24 and to receive the associated test results from the instrument 24. All control functions can be randomly initiated under control of scheduling software and logic to match pending requisition requirements and current instrument status conditions.

The external computer can send patient requisitions to the workstation either individually or in ring segment groups. The workstation can send test results to the external computer.

The control system associated with chemistry instrument 24 includes several dedicated microprocessors and programmable memory devices. They individually operate the system components as prioritized by scheduling software residing in the instrument CPU board. The workstation 30 includes monitoring means for maintaining a current record of the amount of liquid in containers on the sample/reagent tray 15. Controlling software associated with the microprocessors causes the mechanical components of the chemistry instrument 24 to carry out all operations efficiently and effectively without operator intervention, using a random sequence of movements dictated by outstanding test requirements.

The arrangement of operational stations along the arcuate path of pipette 18 permits transfer of liquids from a draw tube 27 at the sample access station B to a well 36 at a container access station $C_1$ or $C_2$ on the sample/reagent tray or from a well 36 to a cuvette 10 at the cuvette access station A on turntable 11. Alternately, pipette 18 can transfer sample diluents (buffers) from the reagent bottles 25 at container access stations $C_3$ or $C_4$ on the sample/reagent tray 15 to a well 36 at a container access station $C_1$ or $C_2$. In addition, it can transfer liquids from one well 36 to another, or from a cup 35 to a well 36 for dilution purposes at container access stations $C_1$ or $C_2$. Direct transfer of reagents from bottles 25 to cuvettes 10 can also take place at cuvette access station A. A wash or pipette alignment procedure can also be periodically accomplished at wash/alignment station D as required. ISE tests are initiated by optional delivery of sample liquids to the ISE station E.

Cuvettes

Figure 6:
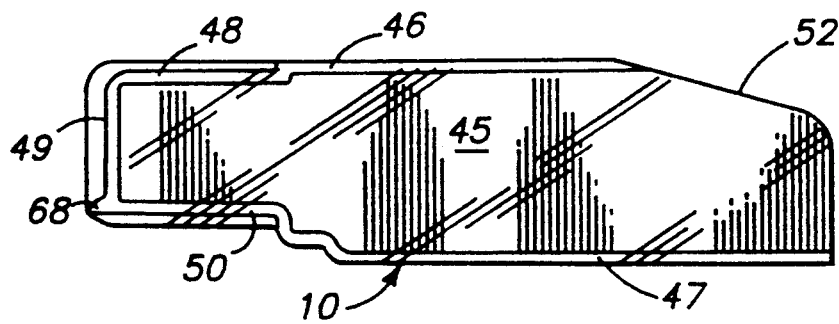
FIG. 6 is a side elevation view of a cuvette.
Figure 7:
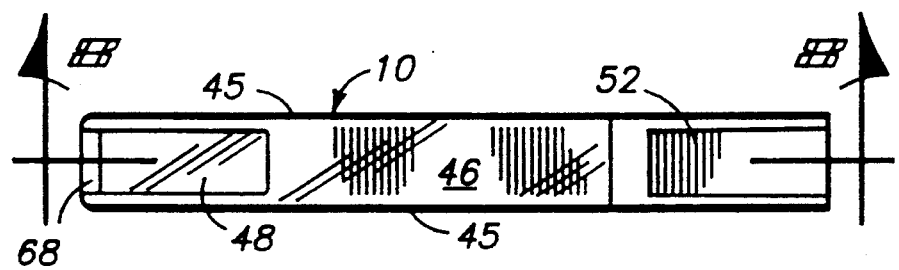
FIG. 7 is a top view.
Figure 8:
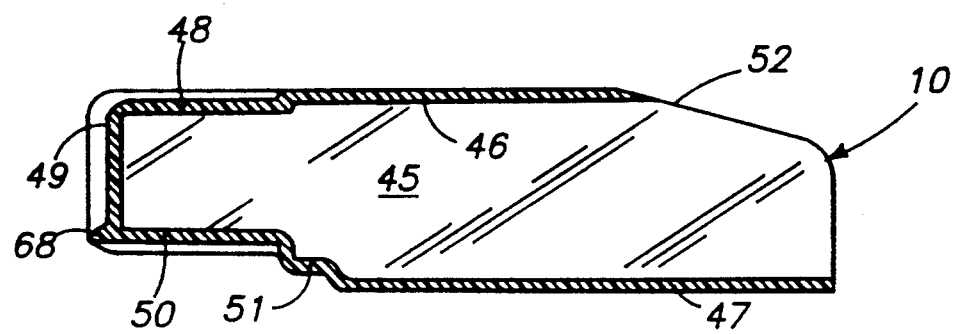
FIG. 8 is a sectional elevation view taken along line 8—8 in FIG. 7.

The disposable cuvettes 10 designed for use in turntable 11 are illustrated in detail in FIGS. 6–8. A complementary cartridge 40 for handling and storing the cuvettes is shown in FIGS. 9 and 10.

Cuvettes 10 are molded from a suitable transparent rigid plastic material that is liquid impervious and inert to the liquids which they are to contain. The cross-sectional configuration of each cuvette is rectangular.

Each cuvette 10 includes two identical side walls 45 having parallel top and bottom edges. The straight top and bottom edges along each side wall 45 longitudinally overlap one another to facilitate stacking of the cuvettes in abutting parallel positions. Side walls 45 are transversely joined by parallel spaced top and bottom walls 46 and 47.

One end of each cuvette 10, termed its "upper end", includes an opening 52 between the end edges of the side walls 45. Opening 52 provides access to the interior of cuvette 10 for receipt of liquids. The edges of side walls 45 that form the opening 52 include angular edges intersecting the straight top edges of the respective side walls 45. The angular edges assume horizontal orientations when positioned in turntable 11 (FIG. 12). The end edges along the opening 52 are perpendicular to the top and bottom walls 46 and 47. The opening of cuvettes that are pre-loaded with reagents or other materials before use in the chemistry instrument 24 can optionally be sealed by a suitable film or other cover (not shown) capable of being pierced by the descending tip of pipette 18.

The opposite end of each cuvette 10, termed its "lower end", includes perpendicular optical surfaces for transmission of light in conjunction with operation of the optical system 14. These surfaces include top, end and bottom optical surfaces 48, 49 and 50, respectively. Each optical surface area is slightly recessed inwardly from the outer edges of side walls 45 to protect the optical surfaces from abrasion or contact during handling.

The lower end of each cuvette 10 has a transverse protruding wall 68 extending across the two side walls 45. Wall 68 provides a continuous transverse surface for abutment of the upper end of an adjacent cuvette 10 when one cuvette pushes another into position within turntable 11.

A small downwardly-facing recess 51 is provided within the bottom wall 47 of each cuvette 10 next to the inner end of lower optical surface 50. The recess 51 serves as a detent in conjunction with a spring-biased enlargement (see FIG. 12) that yieldably holds cuvette 10 within a receiving compartment on the turntable 11.

The cuvettes are preferably packaged within elongated disposable cartridges 40 (see FIGS. 9 and 10). The parallel stacked cuvettes 10 face oppositely at the respective ends of cartridge 40. The cartridge 40 is designed for insertion into the open slots of a receiving cuvette magazine 75 shown in FIG. 18.

The cuvette cartridge 40 is formed from a C-shaped channel 41 having interior surfaces complementary to the exterior shape and size of the individual cuvettes 10. Cartridge 40 can be formed from any suitable stiff, resilient plastic sheet or can be extruded in the shape illustrated in FIGS. 9 and 10. Its purpose is to facilitate handling and storage of the large quantities of cuvettes 10 required by each chemistry instrument 24. It expedites manual entry of cuvettes 10 into the storage magazine 75.

Cuvettes 10 fit transversely within the elongated channel 41 in abutting parallel positions within two groups. Each group of cuvettes 10 at the respective ends of cartridge 40 is identical to a full stack of cuvettes within the receiving magazine 75. Two pairs of inwardly bent stops 42 near the center of cartridge 40 limit inward motion of cuvettes along the length of the magazine. Outward movement of cuvettes at each end of the cartridge 40 is resisted by smaller end stops 43. The stops 43 are bent inwardly to partially intersect the path of cuvettes 10 as they exit the cartridge 40.

Turntable

Figure 11:
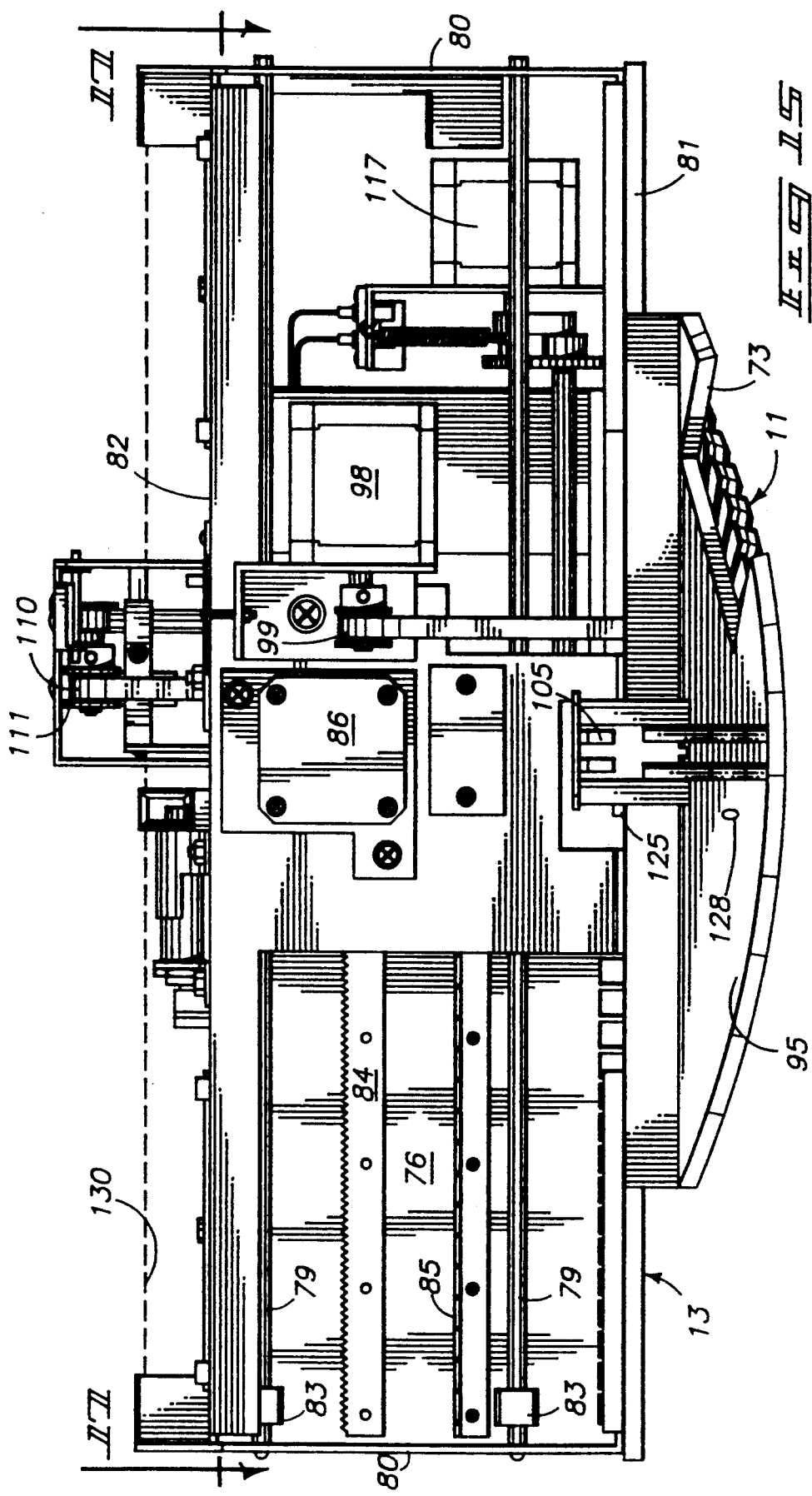
FIG. 11 is a plan view of the cuvette turntable.
Figure 20:
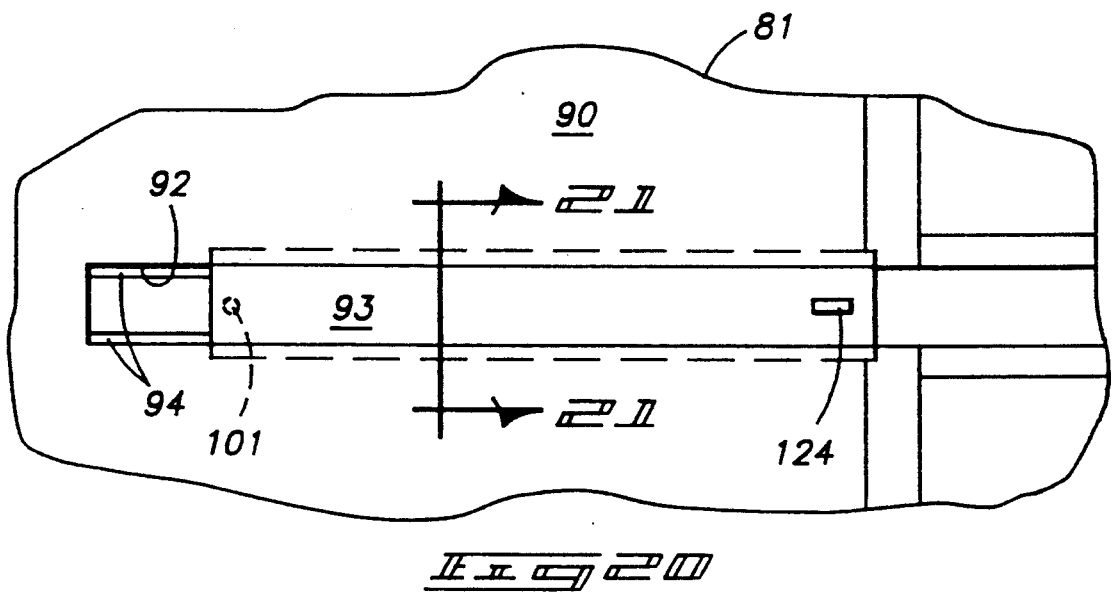
FIG. 20 is an enlarged fragmentary view taken along the cuvette-receiving slot as seen along line 20—20 in FIG. 19.
Figure 21:
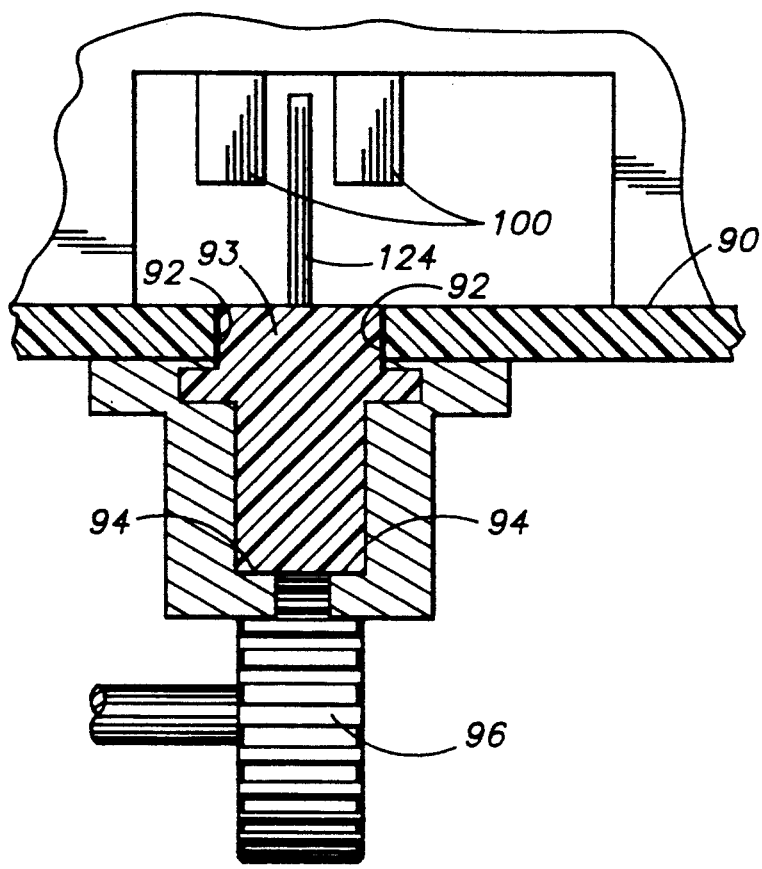
FIG. 21 is a sectional view taken along line 21—21 in FIG. 20.

Turntable 11 is detailed in FIGS. 11-13. It includes a circular, radially-slotted wheel rotatably mounted about a vertical axis X—X (FIG. 13). The outer periphery of the turntable 11 presents a series of equiangularly spaced radial compartments 53. Each compartment 53 individually receives a cuvette 10 in the manner shown in FIG. 12.

Each compartment 53 includes a radial slot having an interior cross-sectional shape and size that complements the exterior cross-sectional shape and size of a cuvette 10. The compartments 53 are arranged about turntable 11 at an angle such that the angular upper edge of each cuvette opening will be oriented horizontally. The angular upper edge is also perpendicular to the axis X—X. The angular nature of each compartment also positions the optical end of each cuvette 10 at a lower elevation than opening 52, assuring that liquids in each cuvette will not spill, even while turntable 11 is stationary.

An axial slot 54 intersects each compartment 53 across its outer end. Slots 54 extend through the upper and lower surfaces of the turntable 11. They provide light access to the optical surfaces 48-50 of cuvettes 10. Slots 54 permit passage of light through the individual cuvettes 10. They are used in conjunction with operation of the optical system 14 to facilitate photometric testing of cuvette contents while within the turntable 11.

The cuvettes are yieldably held within the radial compartments 53 by spring 55 (FIGS. 12, 13). The outer ends 61 of the longitudinal springs 55 are enlarged to enable them to fit within the recesses 51 formed in the cuvettes 10. The spring ends 61 radially position each cuvette 10 within the respective turntable compartments 53.

Springs 55 also serve as interior supports within compartments 53. They yieldably maintain the top walls 46 of cuvettes 10 in engagement with the upper inside surfaces of the compartments 53. The cover 59 about turntable 11 is fabricated of an electrically conductive plastic material. Springs 55 maintain firm surface-to-surface contact between the top wall 46 of each cuvette 10 and the interior surface of cover 59. This provides effective heat transfer to each cuvette to reduce the time required to warm it in preparation for receipt of a test sample. The cover 59 can be heated as the turntable 11 is rotated, using an adjacent stationary source of controlled heat (not shown).

Cuvettes 10 held within the turntable 11 are individually accessible and remain open for reception of samples and reagents as required by requisitioned assays. Liquids are introduced through the openings 52 of the respective cuvettes 10 by operation of probe arm 17 and pipette 18 at the previously-identified cuvette access station A. All incubation of samples involved in an assay occurs within cuvettes 10 in the turntable 11.

The upper surface of the supporting central plate 56 on turntable 11 has a plurality of tapered radial guide surfaces 57 formed about it. Surfaces 57 are centered between each radial compartment 53 and are obliquely aligned with the respective compartments 53. They are used to index turntable 11 during reception of incoming cuvettes. This will be described in relation to the interaction between the cuvette dispenser module 13 and turntable 11.

As can be seen in FIG. 12, the turntable 11 holds cuvettes 10 in elevationally tilted radial positions. Their openings 52 are exposed for reception of liquid materials. Their optical surfaces 48, 49 and 50 are exposed through slots 54 for transmission of light as required by operation of optical system 14.

Turntable 11 is rotatably supported about a stationary vertical shaft 62 (FIG. 13) fixed to the supporting framework of the chemistry instrument 24. It is rotated by peripheral gear teeth 63 that are drivingly engaged with a motor-driven gear (not shown) operatively powered by motor 12.

Indexing of turntable 11 is accomplished by a circular slotted rim 60 that rotates between a sensor 74 on the framework of the chemistry instrument. A rotational "home" position is defined be a depending flag 129 and a second sensor 139.

Cuvette Delivery Module

The cuvette delivery module 13 is located across the left hand end of the enclosure for the chemistry instrument, as shown in FIG. 3. A plan view of the cuvette delivery module 13 is illustrated in FIG. 14. It is further illustrated in FIGS. 15-23. It overlies turntable 11 at an oblique angle aligned with the compartments 53 (see FIG. 19).

Cuvette delivery module 13 provides automated storage for a plurality of stacks of cuvettes 10 delivered to it from manually-inserted cartridges 40. The cuvettes 10 are stored in parallel upright stacks within a longitudinally shiftable magazine 75. The magazine 75 is separately illustrated at FIG. 18.

Cuvettes discharged from a selected stack within magazine 75 are individually inserted into a selected compartment 53 on the turntable 11. Insertion of a cuvette 10 into a turntable compartment 53 in turn ejects the cuvette 10 previously within it (see FIG. 19). Ejected cuvettes can be temporarily stored within a rigid or flexible container (not shown) on the framework of the chemistry instrument 24. The receiving container should be upwardly open, allowing the ejected cuvettes 11 to drop freely into it from the turntable 11.

Magazine 75 can randomly access individual cuvettes from the lower end of any one of its multiple stacks. This capability is of particular value when stacks of pre-loaded cuvettes containing differing reagents are stored in magazine 75. When using only empty stored cuvettes 10, the stacks of cuvettes within magazine 75 will be accessed in sequence. All of the cuvettes in a stack will be delivered to turntable 11 before a subsequent stack is used.

Magazine 75 is an elongated, rectangular, box-like structure including transversely spaced side walls 76 and 77. Walls 76 and 77 support opposed inner upright walls 78. The inner walls 78 define a series of upright slots. Each slot has a width and a thickness complementary in size to the corresponding dimensions of a cuvette cartridge 40. The slots are therefore sized to complement the exterior length and thickness of the stacked cuvettes 10. The stacked cuvettes 10 fit loosely within the receiving slots. They are fed downwardly within the slots for eventual individual discharge at the bottom of each stack.

The stationary support for the movable magazine 75 is fixed within the hinged cover 34 of the exterior enclosure for the chemistry instrument 24. It includes a base 81 and attached vertical end walls 80. An arcuate hood 95 is integral with base 81. It covers most of the protruding portions of turntable 11. It is interrupted about a portion of its periphery by an opening 73 to expose an arcuate section of the turntable 11, as seen in FIGS. 14–17.

Hood 95 has an open aperture 128 formed through it. Aperture 128 is positioned at the cuvette access station A shown in FIG. 3. Pipette 18 can freely pass through aperture 128 to locate its lower end or tip within the opening 52 at the upper end of an indexed cuvette 10 on turntable 11 for discharge of fluid.

Magazine 75 is covered by a top wall 82 arranged between the end walls 80 in close proximity to the upper ends of the magazine slots. The top wall 82, which can include removable access panels, prevents cuvettes from falling from the magazine when the cover 34 of the enclosure is lifted about its hinges.

Magazine 75 is longitudinally guided on a pair of horizontal rods 79 extending between the end walls 80. Side wall 76 of magazine 75 has spaced bushings 83 that slidably support magazine 75 along the horizontal rods 79.

An exterior rack 84 along the outer surface of the magazine wall 76 imparts longitudinal motion to it. The longitudinal position of magazine 75 relative to the module base 81 is controlled by operation of a stepper motor 86 that drives magazine 75 through a gear 87 in mesh with rack 84 (see FIG. 19). Motor 86 is fixed to an upstanding side plate 88 at the center of module 13.

A longitudinal indexing strip 85 along the wall 76 of magazine 75 is periodically slotted to facilitate optical indexing of magazine 75 relative to its supporting structure within the cuvette delivery module 13. Plate 88 mounts a sensor 89 that straddles the indexing strip 85 to detect the positions of the slots in indexing strip 85. Associated electronic components for the sensor 89 can be provided on a circuitboard shown at 91.

Cuvettes 10 located within magazine 75 freely rest on a smooth planar upper surface 90 presented across the module base 81. The surface 90 is interrupted only by a central transverse slot 92 through which the lowermost cuvette 10 within a stack aligned above it within magazine 75 is delivered for entry into a compartment 53 in turntable 11 (See FIGS. 19, 22 and 23).

Slot 92 is closed or opened by movement of a flush-mounted ram 93 slidably guided within it. Ram 93 is transversely guided within base 81 for movement along slot 92. It moves between an extended inner position, an outer position, and a cuvette inserting position.

Incoming cuvettes 10 within slot 92 are vertically supported on opposed transverse ledges 94 within the open slot 92 (FIGS. 22, 23). They can then be pushed into an indexed compartment 53 on the turntable 11 by reciprocation of ram 93.

The ram 93 is illustrated in FIG. 19 at a position where it partially closes the opening presented by slot 92 and is pushing a cuvette 10 into a turntable compartment 53. Ram 93 also moves inwardly along the empty slot 92 before it allows a cuvette 10 to drop within slot 92. This causes a pin 101 at its underside to wedge between paired tapered guide surfaces 57 on turntable 11. The wedging action mechanically indexes turntable about axis X—X for accurate reception of a cuvette 10 within compartment 53. The retracted position of ram 93 leaves slot 92 fully open to receive cuvette 10 within it.

The ram 93 is powered by a rotatable gear 96 that meshes with a downwardly facing rack 97 formed along the bottom of ram 93 (FIGS. 19 and 23). Gear 96 is powered by a motor 98 on side plate 88 through interconnecting pulleys and a timing belt 99 as shown in FIG. 15.

Three limits of motion of ram 93 are detected by light sensors 100, 104 and 105, respectively, which detect the position of an upwardly protruding tab 124 at the outer end of ram 93. Associated electronic components for the photocells are mounted on a circuitboard 58.

The normal inoperative position of ram 93 is set with tab 124 at intermediate sensor 104. The sequence of movement by ram 93 involves three distinct phases. After turntable 11 has been angularly indexed by motor 12 to receive a cuvette 11, ram 93 is moved inwardly from the position shown in FIG. 22 until tab 124 is detected by sensor 100. This causes pin 101 to wedge between a pair of tapered guide surfaces 57 to assure that a turntable compartment 53 is accurately aligned with the ram 93 for reception of a cuvette 10. Ram 93 next fully retracts until tab 124 is detected by sensor 105. This allows a waiting cuvette to fall through the open slot 92 and rest on ledges 94. Ram 93 then moves inwardly until tab 124 is again detected by sensor 100, thus inserting a new cuvette into the compartment 53 and simultaneously causing the incoming cuvette to eject the preceding cuvette from the turntable compartment. The downward motion of each stack of cuvettes 10 is monitored by a vertically movable follower 107, described in detail below.

Each end of the complementary cuvette magazines 40 holds a complete stack of cuvettes. The inventory system for the magazine 75 is based upon a manual loading protocol where individual stacks of cuvettes 10 are to be replenished only after they have been totally depleted.

Figure 2:
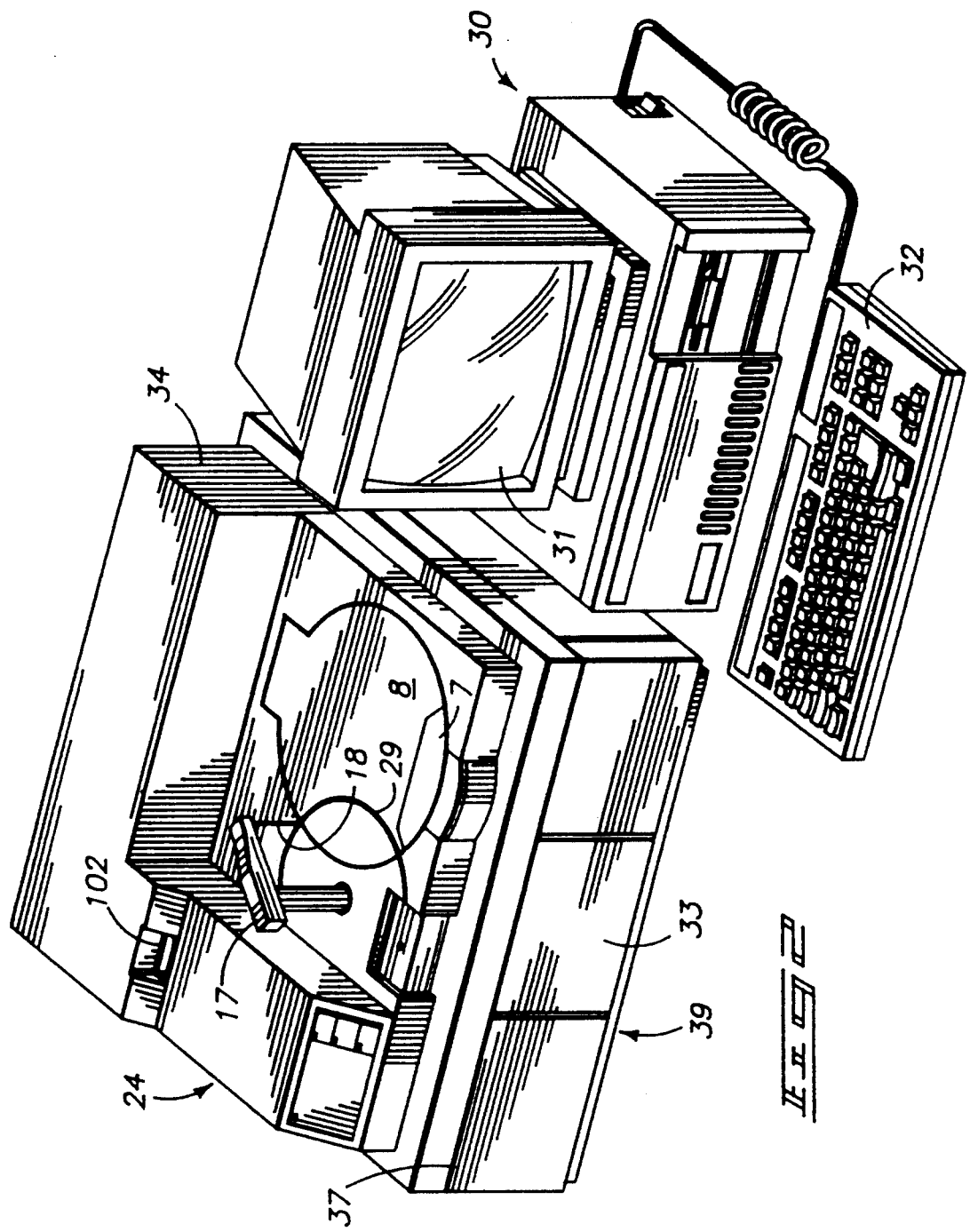
FIG. 2 is a perspective view of the analyzer.

One end of a cuvette magazine 40 can be manually inserted into the cuvette delivery module 13 through a slotted guide 102 formed through the enclosure cover 34 (see FIGS. 2 and 3). The guide 102 is transversely intersected by a solenoid-controlled stripper 103 shown in FIG. 14 that blocks entrance of cuvettes until they are required. Retraction of the normally-extended stripper 103 is enabled only when a photocell assembly 126 trained through a slot in guide 102 detects the presence of a cuvette cartridge 40. Actual retraction of stripper 103 is controlled by software instructions from workstation 30, which is programmed to permit refilling of magazine 75 only when a magazine slot under the guide 102 is empty. Retraction of stripper 103 is verified by a photocell assembly 127 mounted on top wall assembly 82, which straddles an extension pin 106 integral with stripper 103.

The elevation of photocell assembly 126 is lower than that of the stripper 103. Thus, the incoming end of cartridge 40 cannot pass the stripper and operate photocell assembly 104 if it is facing improperly within the slotted guide 102. Its lower edge will first abut the upper surface of stripper 103. This provides a mechanical interlock to assure that cartridge 40 and cuvettes 10 within it are not inserted into magazine 75 in a backwardly-facing orientation.

If oriented properly within the slotted guide 102, an incoming cuvette cartridge 40 can be manually pushed through the aligned slot within magazine 75 until its lower end abuts the planar upper surface 90. A photocell sensor 125 directed across surface 90 then detects the fully inserted position of the cartridge 40 and causes the stripper 103 to be extended to its normal position across guide 102. The shaft of stripper 103 then fits between the open legs of the cuvette cartridge 40 in the area between its center stops 42.

Cartridge 40 is removed from within magazine 75 by manually lifting it. The extended end of stripper 103 intersects the location of cuvettes 10 within the legs of the C-shaped channel 41. It prevents their upward movement and causes them to remain in a stacked arrangement within the selected vertical slot of the receiving magazine 75.

Inventorying of cuvettes by workstation 30 is based upon an assumption that a full stack of cuvettes 10 will be supplied to magazine 75 during each loading sequence. The controlling software can maintain information identifying the slots within the magazine 75 that contain full stacks of cuvettes 10. It is therefore necessary only to monitor the partial stack of cuvettes being delivered to the turntable 11 during current use of the chemistry instrument 24 and to measure the height of each stack of cuvettes within magazine 75 at machine startup to always provide complete inventory information. These functions are accomplished by a vertically movable follower 107 (see FIG. 19).

The follower 107 is slidably guided by a supporting bracket 108 fitted about two upright rods 109. This support arrangement for follower 107 can be seen in FIG. 16. Follower 107 can be moved vertically between a normal elevated position clear of magazine 75, as shown in dashed lines at the top of FIG. 19, and a lowered position at which it rests upon the uppermost cuvette 10 in a selected stack within magazine 75, as also illustrated in FIG. 19.

Follower 107 and bracket 108 are moved vertically by a timing belt 110. Bracket 108 is clamped to one flight of the belt 110, which is entrained over upper and lower pulleys 111, 112. Follower 107 always remains in a horizontal position, thereby resisting any tendency of the stacked cuvettes 10 beneath it to assume an angular orientation within the confining walls of the slots within magazine 75.

Engagement of follower 107 with the uppermost cuvette 10 in a stack is detected by the resulting torsional forces exerted on pulley 112 through interconnecting belt 110. Pulley 112 is mounted to an extended shaft 113 leading to a driving motor 117. Cuvette engagement can be accommodated by slippage of disengagement of the driving connection between motor 117 and follower 107, or by stalling operation of the motor.

A printed circuitboard 130 is provided across the remaining side of the cuvette delivery module 13 and mounts the electronic components associated with it. The details of the printed circuitboard 130 are not shown. It is to be understood that the electronic controls for the various motors, sensors, and solenoids will be interconnected in the usual manner to perform the functions of the module as described.

Optical Test System

FIGS. 22 and 23 illustrate the physical arrangement of the components that make up optical system 14, which is located directly next to turntable 11. FIG. 23 is a diagrammatic view showing the light paths involved in providing electronic measurement of absorbance as a function of light transmitted through the test samples in the individual rotating cuvettes 10 or fluorescence polarization as a function of emissions produced by test samples within individual cuvettes 10 in response to light excitation.

Figure 4:
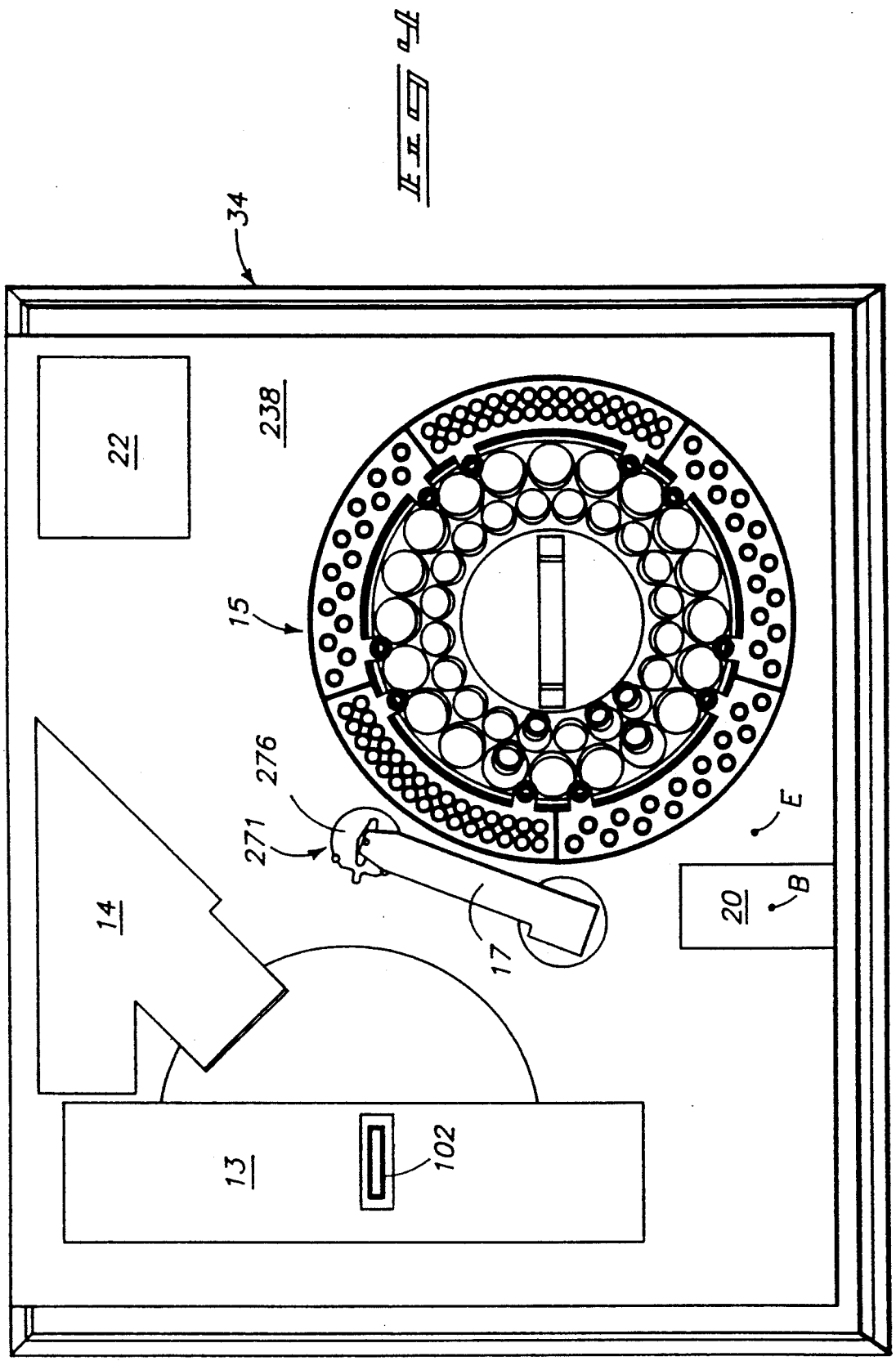
FIG. 4 is a plan view of the chemical instrument enclosure with the cover removed.
Figure 5:
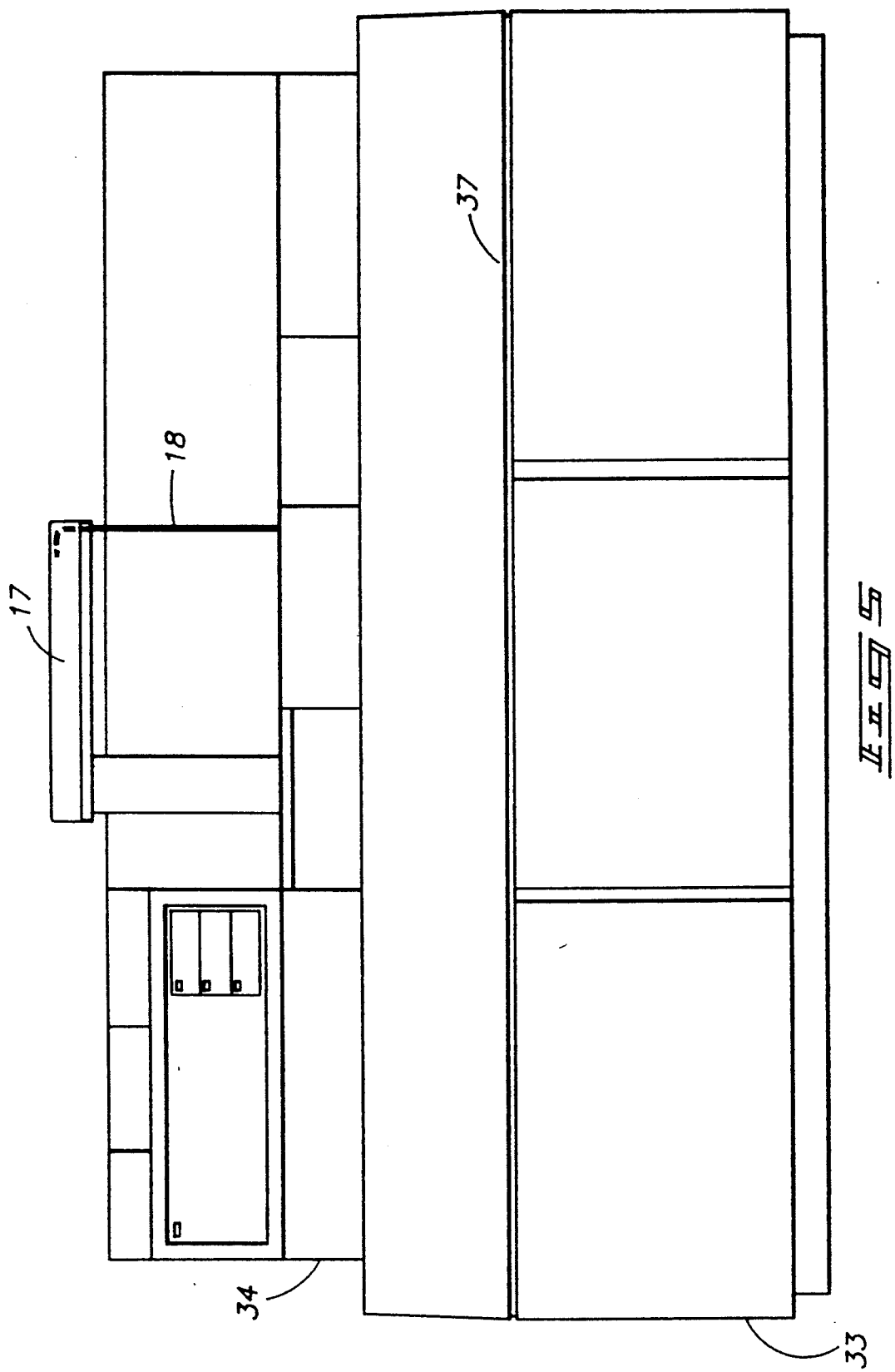
FIG. 5 is a front elevation view of the enclosure.

The optical system is located within a molded light-proof enclosure 192. The exterior of the enclosure includes a transverse recess 193 that extends fully across the width of the enclosure. The outer periphery of turntable 11 is positioned to rotate through recess 193 within the arcuate opening 73 in hood 95 of the cuvette delivery module 13. The position of turntable 11 with respect to the optical system 14 is shown in FIG. 4. It is more specifically illustrated in dashed lines in FIG. 22.

The inclined orientation of recess 193 complements the inclined arrangement of the cuvettes 10 about the periphery of turntable 11. Recess 193 within the optical system enclosure overlaps the previously-described slots 54 in turntable 11, which provide exterior exposure to optical surfaces 48, 49 and 50 of each cuvette 10.

The general features of the optical test system are shown in the diagram presented in FIG. 23. Recess 193 is has an upper light window 194, an opposed lower light window 195 and an end light window 196. Windows 194 and 195 permit transmission of light through the upper and lower optical surfaces 48, 50 of each cuvette 10 for absorbance tests. Light window 196 transmits fluorescent light emissions from within each cuvette 10 through its end optical surface 49.

A conventional pulsed Xenon lamp 190 is used in the optical system 14 as an intermittent high intensity light source for both absorbance and fluorescence polarization testing purposes. Its excitation is timed to coincide with the time of passage of each cuvette 10 through the recess 193. A lamp power supply 188, also of conventional design, is included in the chemistry instrument 24 to provide required electrical power to the lamp 190.

The optical system will be described first with respect to the absorbance subsystem used for detecting transmission of different light wavelengths during analysis of reaction mixtures within cuvettes 10.

Light pulses from lamp 190 are received through a circular infrared filter 197. The resulting light path is surrounded by a ring of reference diodes 236 that measures incoming light intensity. The path of the filtered light entering the optical system enclosure is then turned 90° by a diagonally placed mirror 200. This first light path leads to a first detector 215 for monitoring the intensity of light absorbed by a test sample within a cuvette 10 in response to light passing along the first light path through the pair of optical surfaces 48, 50 at the top and bottom of the cuvette.

Light from lamp 190 is initially focused across the center plane of each cuvette 10 located within recess 193 by two plano-convex lenses 202 and 203 provided in an upper optics module. A large lens aperture (not shown) is located directly adjacent to lens 202 and restricts the passage of light to a defined circular aperture area.

Light passing through the cuvettes 10 within recess 193 is again focused at a transverse slit aperture 209. The required focusing is accomplished by use of paired plano-convex lenses 207 and 208 in the lower optics module shown in FIG. 23.

The narrow, focused beam of light that passes through slit aperture 209 is directed to a holographic grating 212 within the interior of the enclosure. The holographic grating 212 is positioned at an angle to the axis of the light beam to direct resulting scattered light onto a photo diode array 215 capable of detecting the intensities of light at a plurality of discrete wave lengths. The photo diode array 215 includes a linear pattern of light-receiving diodes arranged across the enclosure at the locations where the monitored frequencies will be scattered by holographic grating 212.

Fluorescence polarization is monitored by use of a second detector 232 aligned along a second light path perpendicular to the first light path and adapted to intersect the third or end optical surface 49 of a cuvette.

To measure fluorescence polarization that results from light excitation of the cuvette contents, a movable fluorescence excitation filter 205 having a polarized coating at one surface must be inserted between lamp 190 and the cuvettes 10 in turntable 11.

Monitoring of fluorescence polarization requires measurement of emitted fluorescence at two different orientations. This can be effectively accomplished by use of the well-known arrangement of passing the fluoresced light through a polarizer to a detector and measuring one component, and then rotating the polarizer 90° and measuring the second component.

As shown in FIG. 23, the apparatus used for monitoring intensity of fluorescence polarization includes a rotatable polarizer 266 and a fluorescence emission filter 264 coaxially aligned along a second light path. The light path leads to a receiving photo-multiplier tube 232 that produces a signal indicative of the intensity of the received fluorescence at each of the selected angular orientations. Conventional lenses 267 and 268 intensify and focus the emitted light passing through the polarizer 266 and filter 264.

The polarizer 266 is held within a supporting rotatable drum 269 having an external gear driven by a motor 270. Idler gears can be interposed between the motor 270 and the exterior of drum 269 as required.

Drum 269 is turned about its axis between two angular stops that physically limit its rotation to 90°. As one example, the drum 269 might be slotted about 90° of its periphery and a pin projecting into the slot would define the limits of its rotational motion about its central longitudinal axis.

The exterior of the enclosure also includes support posts 235 for additional printed circuitboards that mount electronic devices associated with the optical analyzing system.

FIG. 23 graphically illustrates the path of light through the optical system. The single unit can be readily converted from an absorbance system to a fluorescence polarization system. This is accomplished by placement of the excitation filter 205 either within or outside the light beam pulsed into the enclosure by operation of lamp 190. In operation, it is anticipated that both absorbance and fluorescence polarization readings will be taken of samples within selected cuvettes 10 in the turntable 11 during each of its operational cycles. The actual nature of the tests conducted will depend upon the analytical results required by any particular tests being carried out during each turntable cycle.

Overview of Method

The method for operating the chemistry analyzer 24 basically entails several randomly selectable steps. Operation of the chemistry instrument 24 is timed about a repetitious sequence of cyclically transferring liquid from any selected container on the sample/reagent tray 15 to any selected cuvette 10 on the turntable 11, mixing liquids within the cuvettes on the turntable by turning it about the first axis, and rotating the turntable about the first axis. The timing of these steps are graphically depicted in FIG. 12.

The operational cycles of all components are timed to a repetitious cycle of operation of turntable 11. The turntable 11 is held stationary by motor 12 for a period during which a disposable cuvettes 10 can be delivered to the turntable 11 by operation of the cuvette delivery module. This in turn discharges a spent cuvette into a disposal container in the instrument. The turntable 11 is sequentially indexed to a stationary angular position about the first axis, shown at X—X (FIG. 13), with a selected cuvette 10 positioned at a cuvette access station A. It is then turned about the axis while mixing or centrifuging the contents of cuvettes 10 mounted to it.

As the contents of cuvettes 10 are being centrifuged within turntable 11, the step of analyzing their contents at a location next to the turntable takes place within the optical system. Following fluorescence polarization tests, the mechanically movable filter 205 is repositioned and data is transmitted from the optical testing module while turntable 11 is stationary.

Liquid samples and reagents are supplied to turntable 11 by indexing the sample/reagent tray 15 about a second axis parallel to and spaced from the first axis to a stationary angular position with a selected container positioned at a container access station C. By moving probe arm 17 and pipette 18 along an arcuate path centered about a third axis that is parallel to the first axis and intersecting both the cuvette access station A and the container access station C, the chemistry instrument 24 can selectively transfer liquids from containers positioned on the tray 15 at the container access station C to cuvettes 10 positioned on the turntable 11 at the cuvette access station A. The workstation 30 is programmed so the step of moving the pipette 18 provides randomly accessible transfer of liquid from any container on the tray to any cuvette on the turntable in the time in which the turntable 11 is stationary during each cycle of operation.

An operator can add new cuvettes 10 to the chemistry instrument 24 at any time by initiating a Hopper access, which is manually entered at the keyboard 32 of workstation 30. When a cuvette insertion is requested, the instrument will position the cuvette magazine 75 of the cuvette delivery module 13 to locate an empty slot within it under the cartridge guide 102 and illuminate an indicator at the front of the chemistry instrument 24.

The operator can then insert a cartridge 40 filled with cuvettes 10. The cuvette delivery module 13 will sense when the insertion has been completed as the cartridge 40 is withdrawn, and will proceed to the next empty slot. This is repeated until there are no more empty slots within the magazine 75 or until the operator terminates the process at keyboard 37. A pause indicator will be visible on monitor screen 31 until the cuvette insertion procedures have been completed.

As the contents of cuvettes 10 are being rotated within turntable 11, the step of analyzing their contents at a location adjacent to the turntable takes place within the optical system 14.

Liquid samples and reagents are supplied to turntable 11 by indexing the sample/reagent tray 15 about a second axis parallel to and spaced from the first axis to a stationary angular position with a selected container positioned at a container access station C. By moving probe arm 17 and pipette 18 along an arcuate path centered about a third axis that is parallel to the first axis and intersecting both the cuvette access station A and the container access station C, the chemistry instrument 24 can selectively transfer liquids from containers positioned on the tray 15 at the container access station C to cuvettes 10 positioned on the turntable 11 at the cuvette access station A. The workstation 30 is programmed so the step of moving the pipette 18 provides randomly accessible transfer of liquid from any container on the tray to any cuvette on the turntable in the time in which the turntable 11 is stationary during each cycle of operation.

In compliance with the statute, the invention has been described in language more or less specific as to methodical features. It is to be understood, however, that the invention is not limited to the specific features described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. A cuvette for use in a chemical analyzer, in which the cuvette is integrally molded from rigid liquid impervious material in a hollow rectangular cross sectional configuration, the cuvette comprising:
   two parallel side walls arranged in transversely spaced positions extending between opposed ends of the cuvette, each side wall having top and bottom edges and two end edges arranged across the respective ends of the cuvette;
   one end of the cuvette having an opening extending across its end edges and continuing between the top edges of the side walls to provide vertical access to the interior of the cuvette for delivery of liquids into the cuvette when it is upwardly inclined relative to the horizontal;
   the remaining end of the cuvette being closed by an end wall formed across the two side walls;
   a top wall joining the end wall and the respective top edges of the two side walls;
   a bottom wall joining the end wall and the respective top edges of the two side walls;
   optical surface areas provided at the remaining end of the cuvette for transmission of light during optical testing of cuvette contents;
   wherein outer surfaces of the optical surface areas are each recessed inwardly from the adjacent edges of the side walls to protect the optical surface areas from abrasion or physical contact.

2. The cuvette of claim 1, wherein the optical surface areas include:
   top and bottom rectangular areas formed respectively across corresponding sections along the top and bottom walls located adjacent to the remaining end of the cuvette, the top and bottom rectangular areas each including inner and outer planar surfaces that are parallel to one another; and
   a rectangular area formed across the remaining end of the cuvette, the rectangular area also including inner and outer planar surfaces;
   the planar surfaces of the top and bottom rectangular areas being perpendicular to the planar surfaces of the rectangular area formed across the remaining end of the cuvette.

3. The cuvette of claim 1, wherein the outer surfaces are planar;
   the end wall at the remaining end of the cuvette further including a transverse protruding ledge flush with the adjacent end edges of the side walls.

4. The cuvette of claim 1, wherein the top and bottom walls include parallel sections leading from the opening at the one end of the cuvette and joined to the top and bottom optical surface areas, respectively;
   the top and bottom optical surface areas each including inner and outer planar surfaces that are parallel to one another and are recessed inwardly from the respective parallel sections of the top and bottom walls.

5. The cuvette of claim 1, wherein the top and bottom walls include parallel sections leading from the opening at the one end of the cuvette and joined to the top and bottom optical surface areas, respectively;
   the top and bottom optical surface areas each including inner and outer planar surfaces that are parallel to one another and are recessed inwardly from the respective parallel sections of the top and bottom walls;
   an end optical surface area formed across the remaining end of the cuvette, the end optical surface area including inner and outer planar surfaces;
   the planar surfaces of the top and bottom optical surface areas being perpendicular to the planar surfaces of the end optical surface area.

6. The cuvette of claim 1, wherein the opening extends completely across the one end of the cuvette.

7. The cuvette of claim 1, further comprising:
   a detent formed along the bottom wall of the cuvette.

8. The cuvette of claim 1, wherein the optical surface areas include:
   top and bottom rectangular areas formed respectively across corresponding sections along the top and bottom walls located adjacent to the remaining end of the cuvette, the top and bottom rectangular areas such including inner and outer planar surfaces that are parallel to one another; and a rectangular area formed across the remaining end of the cuvette, the rectangular area also including inner and outer planar surfaces;

the planar surfaces of the top and bottom rectangular areas being perpendicular to the planar surfaces of the rectangular area formed across the remaining end of the cuvette; and a detent formed at the bottom wall of the cuvette as a downwardly facing recess located adjacent to the bottom rectangular surface.

9. A cuvette for use in a chemical analyzer, in which the cuvette is transparent and is integrally molded from rigid liquid impervious material in a hollow rectangular cross sectional configuration, the cuvette comprising:

two identical side walls having parallel straight top and bottom edges and upright perpendicular end edges, the side walls being transversely joined along their respective top edges by a top wall and along their respective bottom edges by a bottom wall;

one end of the cuvette having an opening formed between the side walls, the opening extending between the end edges of the side walls at the one end and continuing between angular edges intersecting both the straight top edges and the end edges of the respective side walls at the one end of the cuvette to permit entrance of the tip of a vertical pipette into the one end of the cuvette while the side walls are in vertical positions and the angular edges are in horizontal positions with the top and bottom edges inclined at an angle to the horizontal;

the remaining end of the cuvette being closed by an end wall formed across the two side walls; and perpendicular optical surface areas provided at the remaining end of the cuvette for transmission of light during optical testing of cuvette contents, wherein the optical surface areas are recessed inwardly from and parallel to the adjacent edges of the side walls to protect the optical surface areas from abrasion or physical contact, the optical surface areas including:

top and bottom rectangular areas formed respectively across corresponding sections along the top and bottom walls located adjacent to the one end of the cuvette; and a rectangular area formed across the remaining end of the cuvette.

10. The cuvette of claim 7, wherein the top and bottom edges of the side walls longitudinally overlap one another to facilitate stacking of a plurality of aligned cuvettes in abutting parallel positions.

11. The cuvette of claim 10, wherein the end wall at the remaining end of the cuvette further includes a transverse protruding ledge flush with the adjacent end edges of the side walls to provide a continuous transverse surface for abutment of the upper end of an adjacent cuvette when one cuvette longitudinally pushes another.

12. The cuvette of claim 9, further comprising:

a detent formed at the bottom wall of the cuvette as a downwardly facing recess located longitudinally adjacent to the bottom rectangular area.

13. A cuvette package that facilitates storage, handling and insertion of stacked cuvettes for use in a chemical analyzer, comprising:

an elongated cartridge formed from a C-shaped channel;

a plurality of cuvettes transversely stacked in identical abutting parallel positions within the cartridge, each cuvette being integrally molded from rigid liquid impervious material in a hollow rectangular cross sectional configuration and including:

two identical side walls having parallel top and bottom edges and upright end edges, the side walls being transversely joined by a top wall and a bottom wall;

one end of each cuvette having an opening between the end edges of the side walls, the opening extending between the end edges of the side walls at the one end and continuing between angular edges intersecting both the straight top edges and the end edges of the respective side walls at the one end of the cuvette to permit entrance of the tip of a vertical pipette into the one end of the cuvette while the side walls are in vertical positions and the angular edges are in horizontal positions with the top and bottom edges inclined at an angle to the horizontal;

the remaining end of the cuvette being closed by an end wall formed across the two side walls; and optical surface areas provided at the remaining end of each cuvette for transmission of light during optical testing of cuvette contents;

the cartridge having transverse interior surfaces complementary to the exterior shape and size of a stack of the individual cuvettes;

first stop means within the cartridge for limiting motion of a stack of cuvettes in a first direction along the length of the cartridge; and second stop means within the cartridge for resisting motion of the stack of cuvettes in an opposite direction along the length of the cartridge.

14. The cuvette package of claim 13 wherein the cartridge is double-ended and holds two stacks of cuvettes that face oppositely at its respective ends;

the first stop means being located near the center of the cartridge;

the second stop means being located adjacent each end of the cartridge.

* * * * *